United States Patent
Klemm et al.

(10) Patent No.: US 8,484,339 B2
(45) Date of Patent: *Jul. 9, 2013

(54) ADVANCED AVAILABILITY DETECTION

(75) Inventors: Reinhard Peter Klemm, Basking Ridge, NJ (US); Lynne Shapiro Brotman, Westfield, NJ (US)

(73) Assignee: Avaya, Inc., Basking Ridge, NJ (US)

( * ) Notice: Subject to any disclaimer, the term of this patent is extended or adjusted under 35 U.S.C. 154(b) by 440 days.

This patent is subject to a terminal disclaimer.

(21) Appl. No.: 12/724,155

(22) Filed: Mar. 15, 2010

(65) Prior Publication Data

US 2010/0235501 A1    Sep. 16, 2010

Related U.S. Application Data

(60) Provisional application No. 61/160,572, filed on Mar. 16, 2009.

(51) Int. Cl.
*G06F 15/16* (2006.01)

(52) U.S. Cl.
USPC .......................... 709/224; 709/204; 709/228

(58) Field of Classification Search
USPC ................. 709/200–203, 217–227, 228, 204
See application file for complete search history.

(56) References Cited

U.S. PATENT DOCUMENTS

| | | | |
|---|---|---|---|
| 7,424,537 B2 * | 9/2008 | Bennett et al. | 709/227 |
| 7,529,683 B2 * | 5/2009 | Horvitz et al. | 705/1.1 |
| 7,603,464 B2 | 10/2009 | White | |
| 7,689,657 B2 * | 3/2010 | Daniell et al. | 709/206 |
| 7,693,509 B2 | 4/2010 | Miyata | |
| 7,958,453 B1 * | 6/2011 | Taing | 715/744 |
| 7,970,384 B1 * | 6/2011 | Lambert et al. | 455/412.1 |
| 8,082,302 B2 * | 12/2011 | Becker et al. | 709/204 |
| 8,190,705 B2 * | 5/2012 | Bennett et al. | 709/217 |
| 8,358,762 B1 * | 1/2013 | Renner et al. | 379/202.01 |
| 2004/0143603 A1 * | 7/2004 | Kaufmann et al. | 707/104.1 |
| 2006/0004911 A1 | 1/2006 | Becker et al. | |
| 2006/0015609 A1 | 1/2006 | Hagale et al. | |

(Continued)

FOREIGN PATENT DOCUMENTS

| | | |
|---|---|---|
| CN | 1901513 A | 1/2007 |
| EP | 1505529 A1 | 2/2005 |

(Continued)

OTHER PUBLICATIONS

Wheeler, Owen, "GB Application No. GB1004182.0 Office Action Jul. 16, 2010", , Publisher: UK IPO, Published in: GB.

(Continued)

*Primary Examiner* — Moustafa M Meky

(57) ABSTRACT

A method is provided for determining user availability on the basis of the manner in which a person uses (1) a communication terminal or (2) a computing device that is associated with the communication terminal or (3) any combination of (1) and (2). User availability is determined based on: (1) a characteristic of the use of a software application that is running on a computing device, or (2) a characteristic of the use of a feature of software that is running on a communication terminal, or (3) a characteristic of the use of a resource of a computing device, or (4) a characteristic of the use of a resource of a terminal, or (5) a sensor input, or (6) a characteristic of the incoming invitation, or (7) any combination of (1), (2), (3), (4), (5), and (6).

18 Claims, 15 Drawing Sheets

U.S. PATENT DOCUMENTS

| | | | |
|---|---|---|---|
| 2006/0072721 A1* | 4/2006 | Wisniewski | 379/88.22 |
| 2006/0253593 A1* | 11/2006 | Jachner | 709/227 |
| 2007/0004385 A1* | 1/2007 | Horvitz et al. | 455/414.1 |
| 2007/0130260 A1 | 6/2007 | Weintraub et al. | |
| 2007/0186007 A1* | 8/2007 | Field et al. | 709/233 |
| 2008/0133742 A1* | 6/2008 | Southiere et al. | 709/224 |
| 2008/0240384 A1* | 10/2008 | Suryanarayana et al. | 379/88.21 |
| 2008/0261630 A1* | 10/2008 | Wormald et al. | 455/466 |
| 2008/0281783 A1* | 11/2008 | Papkoff et al. | 707/3 |
| 2009/0216725 A1* | 8/2009 | Yaqub | 707/3 |
| 2010/0306327 A1 | 12/2010 | Shinkawa et al. | |
| 2013/0041953 A1* | 2/2013 | Renner et al. | 709/204 |

FOREIGN PATENT DOCUMENTS

| | | |
|---|---|---|
| FR | 2814022 | 3/2002 |
| JP | 2003-271204 | 9/2003 |
| JP | 2005-045724 | 2/2005 |
| JP | 2005-110026 | 4/2005 |
| JP | 2005-110028 | 4/2005 |
| JP | 2005-268954 | 9/2005 |
| JP | 2006-119415 | 8/2006 |
| JP | 2006-229415 | 8/2006 |
| JP | 2006-333040 | 12/2006 |
| JP | 2008-118409 | 5/2008 |
| JP | 2008-160753 | 7/2008 |
| JP | 2008-182465 | 8/2008 |
| WO | 0169432 A2 | 9/2001 |

OTHER PUBLICATIONS

Wheeler, Owen, "GB Application No. GB1004183.8 Office Action Jul. 16, 2010", , Publisher: UK IPO, Published in: GB.

Noll, Joachim, "PCT Application No. PCT/US2010/027396 Jun. 11, 2010", , Publisher: PCT, Published in: PCT.

* cited by examiner

ADVANCED AVAILABILITY DETECTION

CROSS-REFERENCE TO RELATED APPLICATIONS

This application claims the benefit of U.S. provisional application Ser. No. 61/160,572, filed Mar. 16, 2009, entitled Presence Based on the Context or Persona of the Party Being Contacted, which is also incorporated by reference.

FIELD OF THE INVENTION

The present invention relates to communications in general, and, more particularly, to availability detection.

BACKGROUND OF THE INVENTION

The term "availability" in the context of communications refers to whether a user is available to accept incoming invitations to participate in communications sessions. For example, a user may be unavailable to accept telephone calls if the telephone line is busy. In instant messaging, a user is unavailable if the user's online status is set to "busy." In the latter case, online status is set manually through a "Change Online Status" menu which is commonly available in instant messaging clients.

Communication devices use availability information to decide whether to accept incoming communications, alert users of incoming communications, display incoming communications, and other purposes. Availability detection, as implemented in existing applications, reflects either the utilization of communication channels or the express unwillingness of users to participate in communications.

At present, availability detection suffers from at least four drawbacks. First, the "availability" of a user reflects only the user's preferences; it does not account for situations in which a user's availability needs to reflect the preferences of third parties. For instance, in the employment setting, it is desirable for both employees, as well as employers to have a say whether the employees are available. Second, users often forget to manually reset their online status, and consequently, it is difficult to know when one's online status is a true reflection of his or her availability. Therefore, the need exists for a method which addresses these drawbacks to provide improved and more robust communication devices.

Third, present availability detection techniques have limited accessibility. In general, enterprise firewalls are configured to block queries to presence servers in the networks which they protect. Configuring enterprise firewalls to let through communications for the presence servers will provide another venue for attack of the enterprise networks. For this reason, at present, corporations do not provide outsiders with access to internal presence servers. As a result, presence information that is internally available cannot be shared with interested parties who reside outside of the enterprise networks. The need, therefore, exists for a method which would enable the interested parties to receive availability information without compromising the security of the enterprise networks.

And fourth, present availability detection techniques have limited interoperability. Presence servers operate in accordance with specialized communication protocols, such as Jabber, for example. When a person wants to connect to a presence server, that person needs to have a client application that supports the protocol of the presence server; otherwise, the person would be unable to exchange information with the presence server. Requiring users to keep track of what protocols are used by different presence servers is cumbersome. Therefore, the need exists for a method for the delivery of availability information that is independent of specialized communication protocols.

SUMMARY OF THE INVENTION

The present invention addresses the drawbacks of the prior art by providing a method for determining user availability on the basis of the manner in which a person uses (1) a communication terminal or (2) a computing device that is associated with the communication terminal or (3) any combination of (1) and (2).

More specifically, the present invention is for a method in which a communication network node determines user availability based on:
 (1) a characteristic of the use of a software application that is running on a computing device, or
 (2) a characteristic of the use of a feature of software that is running on a communication terminal, or
 (3) a characteristic of the use of a resource of a computing device, or
 (4) a characteristic of the use of a resource of a terminal, or
 (5) a sensor input, or
 (6) a characteristic of the incoming invitation, or
 (7) any combination of (1), (2), (3), (4), (5), and (6).

When the switch receives an invitation for a communication session, the communication network node uses determinations of user availability to take at least one of four (4) actions:
 (1) forward the invitation to a specified recipient,
 (2) decline the invitation,
 (3) select a recipient for the invitation out of a pool of possible recipients, or
 (4) take any other action that is specified in this disclosure.

Stated succinctly, the present invention enables communication network nodes to handle incoming communication session invitations based on availability information for one or more users.

In a first embodiment of the present invention, a switch determines user availability according to a characteristic of the use of a software application that is running on a computing device. If the user is deemed available, the switch forwards incoming invitations to the communication terminal of the user. Otherwise, the switch refuses incoming invitations for that user. When the switch refuses incoming invitations, it takes one of the following actions: (1) the switch transmits a busy signal; (2) the switch transmits a message indicating that the user is unavailable; (3) the switch transmits a message indicating that the user is put on hold; (4) the switch hangs up; or (5) the switch takes any other action that is specified by this disclosure.

It should be noted that the computing device and the communication terminal are two different devices that are associated with each other. That is, there exists some relation between the two devices which is known to the switch. For example, the two devices can be collocated (e.g., a desk set telephone receiver and desktop computer that are located in the same office, etc.), assigned to the same user, connected to related switch ports, have sequential identifiers, and so forth. The manner in which the switch keeps track of device associations is discussed in the detailed description of the invention.

In addition to using a "characteristic of the user of a software application," the first embodiment also uses availability policy rules that specify what characteristics indicate that a user is available. For the purposes of clarity, the term "characteristic of the use of a software application" is defined as any item of information concerning the manner in which a specific software application is used. And furthermore, the term "availability policy" is defined as a set of one or more rules which determine when a user is available for communications.

In one instance of its first embodiment, the present invention determines availability based on one or more web sites that have been visited by a web browser. In accordance with this embodiment of the present invention, the websites serve as a clue whether the user of the web browser is available to accept invitations for communication sessions. For example, if the user visits entertainment web sites such as Movies.com™, this is an indication that the user is using his or her communication terminal for personal entertainment and not in relation to the user's employment. In accordance with an availability policy of this example, when a user is found to be visiting Movies.com™, the user is considered available to participate in communications.

In a second instance of its first embodiment, the present invention identifies one or more keywords which are typed in documents that are open for editing on the user's desktop computer. In accordance with this embodiment, the keywords serve as a basis for determining whether the user is available to take part in communications. For example, and without limitation, if an open document contains Internet slang words such as "LOL," this is an indication that the user is engaged in a personal conversation and not in employment-related matters. Thus, in accordance with the availability policy of this example, when Internet slang words are identified in a document, the user is considered available to participate in communications.

In general, the policies of the above examples consider a user available when the user is not engaged in an employment-related activity. Although, the rationale behind the policies is increasing employee productivity, the scope of the present invention is not limited to any particular set of policies. The policies which the present invention implements are determined by the needs of the users of the invention.

In a second embodiment of the present invention, a switch determines user availability according a characteristic of the use of a component of a software application. The software application is executing on a communication terminal. If the user is deemed available, the switch forwards incoming invitations to the communication terminal. Otherwise, the switch refuses any incoming invitations that are directed to the communication terminal.

For the purposes of this specification "a software application component" is a part of a software application which provides functionality for users of the software application. Software application components are defined by underlying application executable code. Different software application components may share executable code. However, the executable code for one component is not completely identical to the executable code for another component if the two components are to provide different functionalities. Stated succinctly, two different components of the same software application must differ in at least one line of code; either machine executable code or higher-level programming language code.

In accordance with its second embodiment, the present invention identifies specific application components that are, or have been, used. This information serves as a basis for determining whether a user is available to take part in communications. For example, and without limitation, a web browser may comprise a web-conferencing component and an animation component. The web-conferencing component is a plug-in which allows the user to participate in company web conferences. Such conferences are strictly business-related. The animation component allows the user to view videos on Youtube.com™. When the animation component is used, the user of the terminal, on which the browser is running, is most likely engaged in the viewing of Youtube.com™videos for personal entertainment. Consequently, in accordance with an availability policy of this example, the user is considered unavailable to participate in communications.

In a third embodiment of the present invention, a switch determines user availability according to a characteristic of the use of a resource. If the user is deemed available, the switch forwards incoming invitations to the communication terminal of the user. Otherwise, the switch refuses any incoming invitations that are directed to the communication terminal.

For the purposes of this specification, the term "characteristic of the use of a resource" is defined as any information concerning at least one of: (1) whether a particular hardware component or peripheral device of a monitored device is used at all; (2) the load and/or utilization rate of a hardware component of the monitored device; and (3) the load and/or utilization rate of a peripheral device (e.g. a printer, scanner, microphone, headset, etc.) that is connected to the monitored device. The monitored device in question is either the communication terminal of the user or a computing device that is associated with the communication terminal.

In one instance of its third embodiment, the present invention determines availability on the basis of a keystroke rate. In accordance with the availability policy of this embodiment, all incoming invitations to the user to participate in a communication session are declined when the user's keystroke rate exceeds a particular threshold of keystrokes per unit time. The rationale for this policy is that if a user is typing fast, the user is most likely devoting his full attention to preparing a document and he or she is unwilling to be disturbed by incoming communication.

In a second instance of its third embodiment, the present invention determines availability on the basis of a cache miss rate. In accordance with the availability policy of this embodiment, all incoming invitations to the user to participate in a communication session are declined when the cache miss pattern is similar to a cache miss pattern that is specified in an availability policy. The cache miss rate provides information about the type of activity in which the user of a communication terminal is engaged. For example, when a user generates many cache misses, the user is likely engaged in manipulating a large data set, such as a large spreadsheet. In this example, when there are indications that a user is involved in work with spreadsheets, the user is unavailable for incoming communications. Just like the exemplary policies described with respect to the first embodiment, the rule of this example promotes increased employee productivity by ensuring that people are not disturbed when their use of computing resources indicates that they are engaged in a productive activity.

In a fourth embodiment of the present invention, a switch determines user availability according to a characteristic of an incoming invitation to participate in a communication session. If the user is deemed available, the switch forwards incoming invitations to the communication terminal. Otherwise, the switch refuses any incoming invitations that are directed to the communication terminal.

For the purposes of this disclosure, the term "characteristic of an invitation to participate in a communication session" is defined as at least one of (1) information about the user initiating the communication session, (2) topic of the communication session, (3) expected duration of the communication session, and (4) priority rating for the communication session.

In a fifth embodiment of the present invention, a switch selects a recipient for an incoming communication session invitation on the basis of an availability determination for that recipient. The recipient is selected from a pool containing at least two possible recipients. In order to select the recipient, the switch determines the availabilities of the possible recipients and selects the one that is most available. The availability determinations are made in accordance with the methods described with respect to the first four embodiments.

Moreover, in some embodiments, the switch selects the recipient in accordance with a routing policy. For the purposes of this specification, the term "routing policy" is defined as a set of one or more rules which determine how an invitation for a communication session is to be routed. The use of routing policies is further discussed in the remainder of this disclosure.

The present invention addresses the drawbacks of the prior art in four ways. First, some embodiments of the present invention allow user availability to be regulated in a centralized fashion. The use of availability policies to determine whether a user is available, allows employers to have input on the whether their employees are available to take incoming calls. In other words, through the use of availability policies, the present invention allows for determinations of user availability that reflect the preferences of third parties.

Second, some embodiments of the present invention are not dependent on the manual setting of an availability status by users. In these embodiments, user availability is determined automatically, according to availability policies, characteristics of the use of software applications, and others. Therefore, the failure of a user to update his or her availability status will not impact the accuracy of the availability determinations.

Third, some embodiments of the present invention increase the accessibility of presence information that is obtained inside enterprise networks. In these embodiments, presence information is distributed by a switch that is connected to a publicly accessible telephone network. The switch provides availability information to users who connect to it via the telephone network. In this way, presence information that is gathered inside enterprise networks can be channeled to the public without reconfiguration of the firewalls of the enterprise networks.

And fourth, some embodiments of the present invention have an increased interoperability over presence servers that are known in the art. These embodiments transmit availability information in the form of voice or text messages over a telephone network. When the messages are received, the users can view their content by using their communication terminals. In other words, the message recipients are not required to use specialized client applications which the recipients would otherwise need if they were to connect to the presence servers of the prior art.

It is to be understood, that the above embodiments and their instances are provided to better illustrate different aspects of the present invention. They are in no way exhaustive of the full scope of the invention. The following disclosure teaches examples of some embodiments of the present invention in detail.

DETAILED DESCRIPTION

Figure 1:
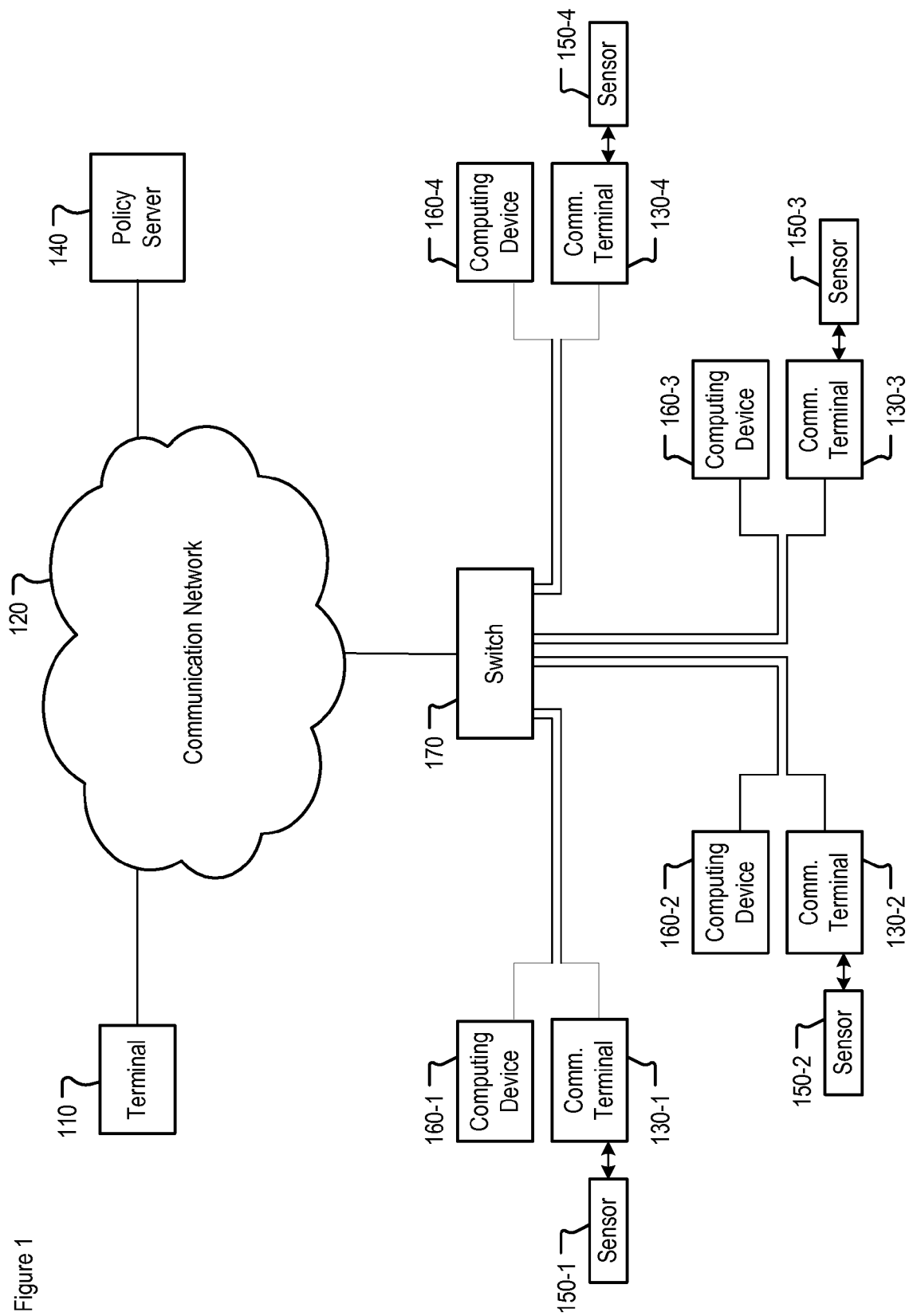
FIG. 1 depicts a schematic diagram of the salient components of the illustrative embodiment of the present invention.

FIG. 1 depicts a schematic diagram of the salient components of the illustrative embodiment of the present invention. The illustrative embodiment comprises terminal 110, communication network 120, switch 170, policy server 140, sensor 150-$i$, terminal 130-$i$, and computing device 160-$i$, where i ∈ {1, 2, 3, and 4}.

Terminal 110 is a desk set telephone receiver. In accordance with the illustrative embodiment of the present invention, terminal 110 is capable of both voice and video communications, but it will be clear to those skilled in the art, after reading this disclosure, how to make and use alternative embodiments of the present invention in which terminal 110 has only a voice capability. Furthermore, it will be clear to those skilled in the art, after reading this disclosure, how to make and use alternative embodiments of the present invention in which terminal 110 is another communication device (e.g. soft phone, cellular telephone, 2-way radio, portable digital assistant, etc.).

Communication network 120 transports signals between terminal 110, switch 170, computing device 160-$i$, and policy server 140. In accordance with the illustrative embodiment of the present invention, communication network 120 is the Internet, but it will be clear to those skilled in the art, after reading this disclosure, how to make and use alternative embodiments of the present invention in which communication network 120 is any type of communication network (e.g. local area network, the Public Switched Telephone Network, SONET, ATM, cellular network, etc.).

Computing device 160-$i$ is a desktop computer that is executing one or more applications, such as, for example, and without limitation, a media player, word processor, spreadsheet software, and others. In accordance with the illustrative embodiment of the present invention, computing device **160-*i* is a desktop computer, but it will be clear to those skilled in the art, after reading this disclosure, how to make and use alternative embodiments of the present invention in which computing device 160-*i* is any type of computing device, such as, for example, and without limitation, a cellular telephone, personal digital assistant, smart phone, and others. Computing device 160-*i* is further described in the discussion with respect to FIG. 2**.

Terminal **130-*i* is a communication terminal. In accordance with the illustrative embodiment of the present invention, terminal 130-*i* is capable of conducting both audio and video telephone calls, but it will be clear to those skilled in the art, after reading this disclosure, how to make and use alternative embodiments of the present invention in which terminal 130-*i* has only a voice capability. Furthermore, it will be clear to those skilled in the art, after reading this disclosure, how to make and use alternative embodiments of the present invention in which terminal 130-*i*** is any type of communication device (e.g. cellular telephone, 2-way radio, portable digital assistant, desk set telephone receiver, etc.).

Policy server 140 is a server which stores availability policy rules and routing policy rules. In accordance with the illustrative embodiment of the present invention, switch 170 receives the policy rules from policy server 140. However, it will be clear to those skilled in the art, after reading this disclosure, how to make and use alternative embodiments of the present invention in which terminal 170 obtains the policy rules from another source (e.g. terminal **130-*i*, etc.). Furthermore, in accordance with the illustrative embodiment of the present invention, the policy rules stored at policy server 140 are specified by the user of terminal 130-*i*, but it will be clear to those skilled in the art, after reading this disclosure, how to make and use alternative embodiments of the present invention in which the availability policy rules are specified by a network administrator, or by the designers of availability detector 247. Although, policy server 140 stores both availability policy rules and routing policy rules, it will be clear to those skilled in the art, after reading this disclosure, how to make and use alternative embodiments of the present invention in which policy server 140** stores only one of the availability and routing policy rules.

Sensor **150-*i* is a plurality of sensors that are capable of supplying data to terminal 130-*i*. Although, in accordance with the illustrative embodiment of the present invention, sensor 150-*i* is a collection of three sensors, it will be clear to those skilled in the art, after reading this disclosure, how to make and use alternative embodiments of the present invention in which sensor 150-*i* includes any number of sensors (e.g. 1, 2, 5, 10, 15, etc.). Furthermore, it will be clear to those skilled in the art, after reading this disclosure, how to make and use alternative embodiments of the present invention in which sensor 150-*i* is connected to the computing device 160-*i*. Sensor 150-*i* is further described in the discussion with respect to FIG. 2**.

Switch 170 is a network switch. In accordance with the illustrative embodiment of the present invention, switch 170 connects communication network 120 to terminal **130-*i* and 160-*i*. However, it will be clear to those skilled in the art, after reading this disclosure, how to make and use alternative embodiments of the present invention in which switch 170 connects terminal 130-*i* to a telephone network such as the public switched telephone network (PSTN) and computing device 160-*i* to a data network, such as the Internet or a local area network (LAN). It will be clear to those skilled in the art, after reading this disclosure, how to make and use alternative embodiments of the present invention in which switch 170** is any other type of network node (e.g. a bridge, gateway, wireless gateway, wireless bridge, etc.).

In accordance with the illustrative embodiment of the present invention, computing device 160-1 is associated with terminal 130-1. More specifically, the association is maintained by means of a table that relates the computing device with the terminal. In accordance with the illustrative embodiment of the present invention, the table relates the media access control (MAC) numbers of the devices, but it will be clear to those skilled in the art, after reading this disclosure, make and use alternative embodiments of the present invention in which the table relates any type of identifiers for the devices (e.g. user-assigned device names, IP addresses, network addresses, etc.). Furthermore, it will be clear to those skilled in the art, after reading this disclosure, how to make and use alternative embodiments of the present invention in which the association between the device is derivative from an association between the ports on a switch to which the devices are connected (i.e. the table relates the numbers of ports on switch 170, rather than specific devices).

Additionally, in accordance with the illustrative embodiment of the present invention, the table is stored at switch 170, however it will be clear to those skilled in the art, after reading this disclosure, how to make and use alternative embodiments of the present invention in which the table is stored elsewhere (e.g. computing device 160, policy server 140, terminal 130-1, etc.).

Figure 2:
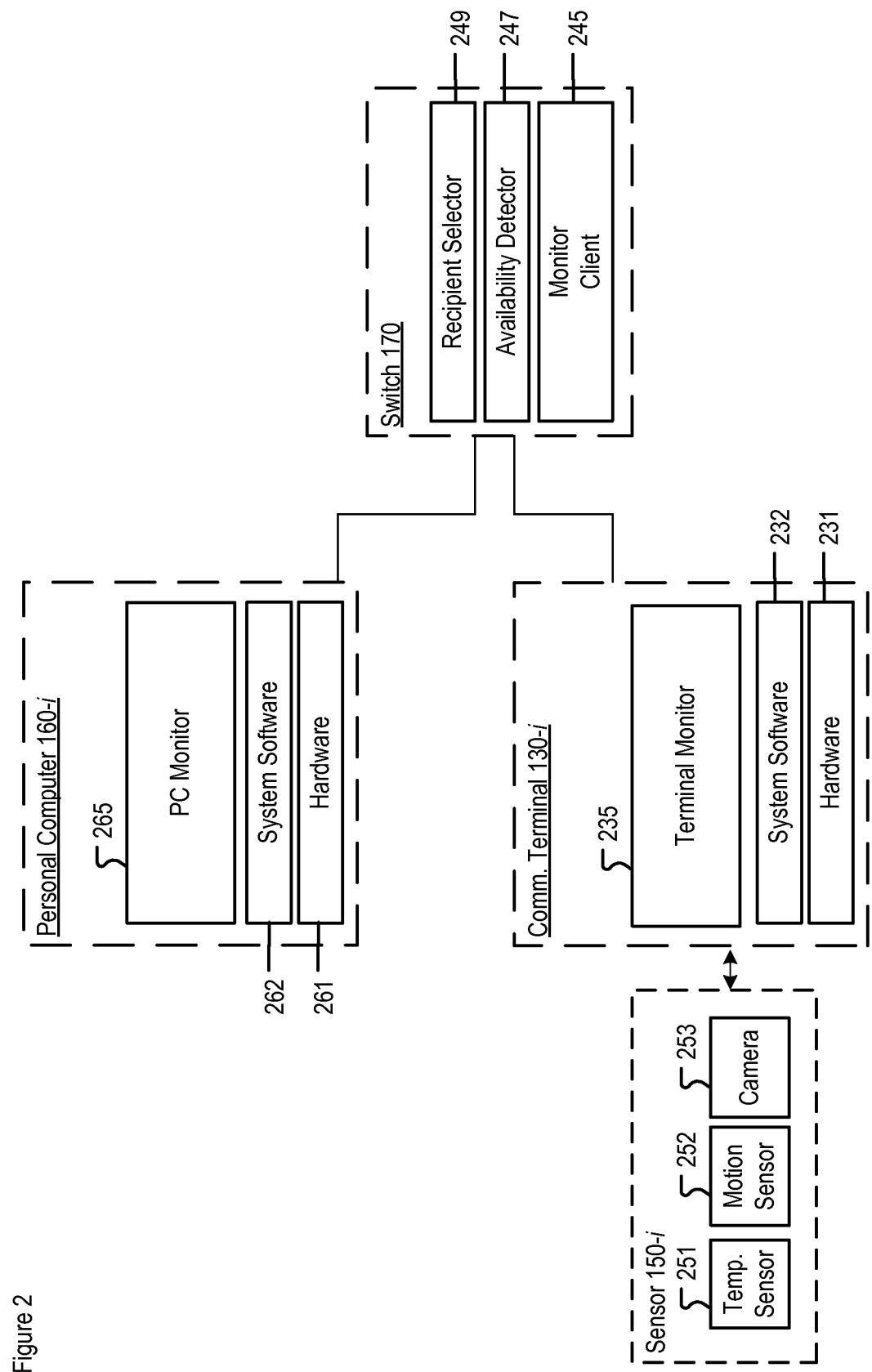
FIG. 2 depicts a schematic diagram of the salient components of the illustrative embodiment of the present invention.

FIG. 2 depicts a schematic diagram of the salient components of the illustrative embodiment of the present invention. The illustrative embodiment comprises sensor **150-*i*, terminal 130-*i*, computing device 160-*i*, switch 170, temperature sensor 251, motion sensor 252, camera 253, hardware 231, system software 232, terminal monitor 235, monitor client 245, availability detector 247, hardware 261, system software 261, and computing device monitor 265**.

Communication terminal **130-*i* comprises hardware 231, system software 232, computing device monitor client 245, and availability detector 247**.

Hardware 231 is the electronic components that comprise terminal **130-*i*, such as, for example, and without limitation, processor (single-core or multi-core), memory, transceiver, network interface, display, sound interface, video interface, etc. Hardware 231 is capable of executing system software and one or more applications. In accordance with the illustrative embodiment of the present invention, hardware 231 is executing computing device monitor client 245, and system software 232. It will be clear to those skilled in the art how to make and use hardware 231**.

System software 232 is an operating system instance that is executing on hardware 231.

Terminal monitor 235 is software for obtaining information about terminal **130-*i***. In accordance with the illustrative embodiment of the present invention, terminal monitor performs at least one of two functions:

i. Obtaining one or more characteristics of the use of a software application component that is running on terminal **130-*i***.
 ii. Obtaining a measurement of the use of one or more resources of terminal **130-*i***.

Monitor client 245 is software that is capable of connecting to computing device monitor 265 and obtaining information about at least one of a characteristic of the use of a software application component that is running on computing device **160-*i*, a measurement of the use of one or more resources of computing device 160-*i*, a characteristic of the use of an application that is running on computing device 160-*i*. Additionally, monitor client 245** is capable of connecting terminal monitor 235 and obtaining information about at least one of a characteristic of the use of a software application component that is running on terminal 130-*i* and a measurement of the use of one or more resources of terminal 130-*i*, and a characteristic of the use of an application that is running on terminal 130-*i*. Also, monitor client 245 is capable obtaining information from sensors 150-*i*.

Availability detector 247 is software for determining whether the user of terminal 130-1 is available to participate in a communication session. The operation of availability detector 247 is further described in the discussion of FIGS. 7-13.

Recipient selector 249 is software for selecting a recipient for incoming invitations for communication sessions. The operation of recipient selector is further described in the discussion of FIG. 15.

Computing device 160-*i* comprises hardware 261, system software 262, and computing device monitor 265.

Hardware 261 is the electronic components that comprise computing device 160-*i*, such as, for example, and without limitation, processor (single-core or multi-core), memory, transceiver, network interface, display, sound interface, video interface, etc. Hardware 261 is capable of executing system software and one or more applications. In accordance with the illustrative embodiment of the present invention hardware 261 is executing computing device monitor 265 and system software 262. It will be clear to those skilled in the art how to make and use hardware 261.

System software 262 is an operating system instance that is executing on hardware 261.

Computing device monitor 265 is software for obtaining information about computing device 160-*i*. In accordance with the illustrative embodiment of the present invention, computing device monitor performs at least one of two functions:

i. Obtaining one or more characteristics of the use of a software application component that is running on computing device 160-*i*.

ii. Obtaining a measurement of the use of one or more resources of computing device 160-*i*.

Figure 4:
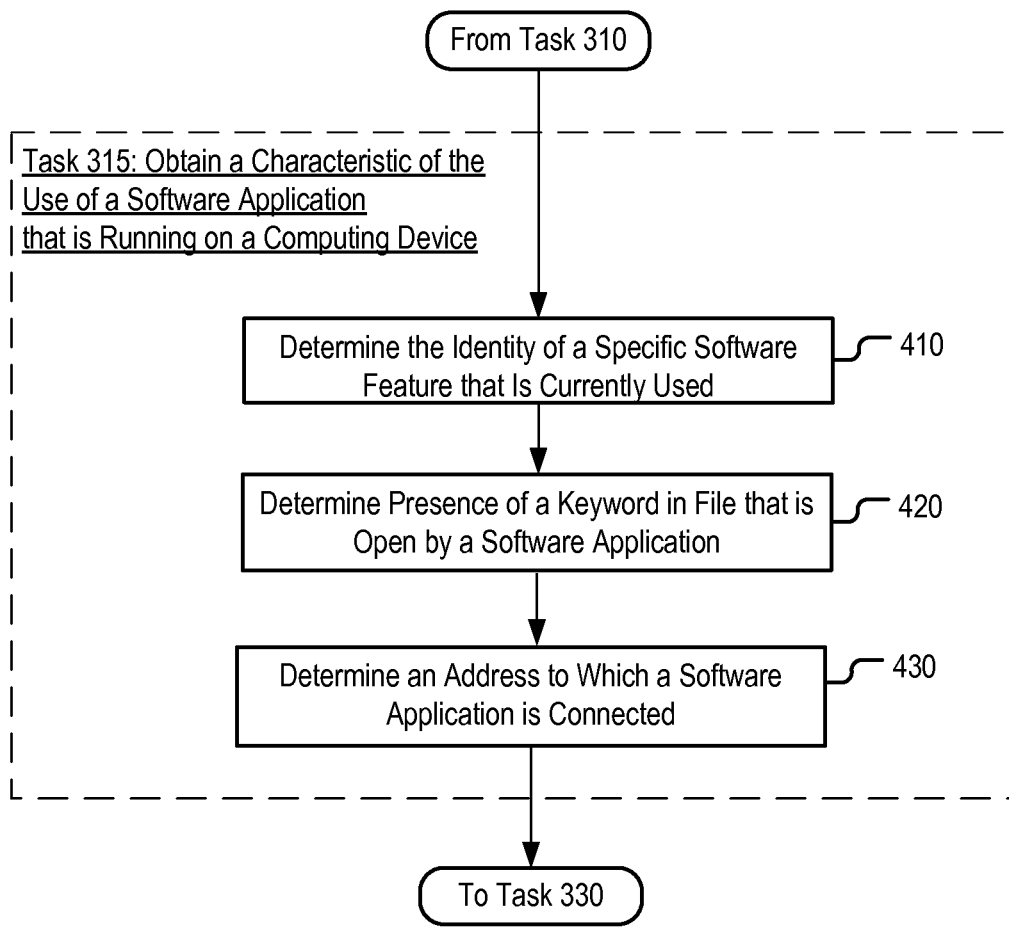
FIG. 4 depicts a flowchart of the execution of the salient subtasks associated with the performance of task 320.

The operation of computing device monitor 265 is described in further detail in the discussion with respect to FIG. 4.

Sensor 150-*i* comprises temperature sensor 251, motion sensor 252, and camera 253.

Temperature sensor 251 is a temperature sensor.

Motion sensor 252 is a motion sensor. In accordance with the illustrative embodiment of the present invention, sensor 252 is an electronic motion detector that uses infra red (IR) technology. However, it will be clear to those skilled in the art, after reading this disclosure, how to make and use alternative embodiments of the present invention in which other sensors are used (e.g. ultrasonic, microwave, hall effect, etc.).

Camera 253 is a video camera. However, it will be clear to those skilled in the art, after reading this disclosure, how to make and use alternative embodiments of the present invention in which camera 253 is a still image camera.

Figure 3:
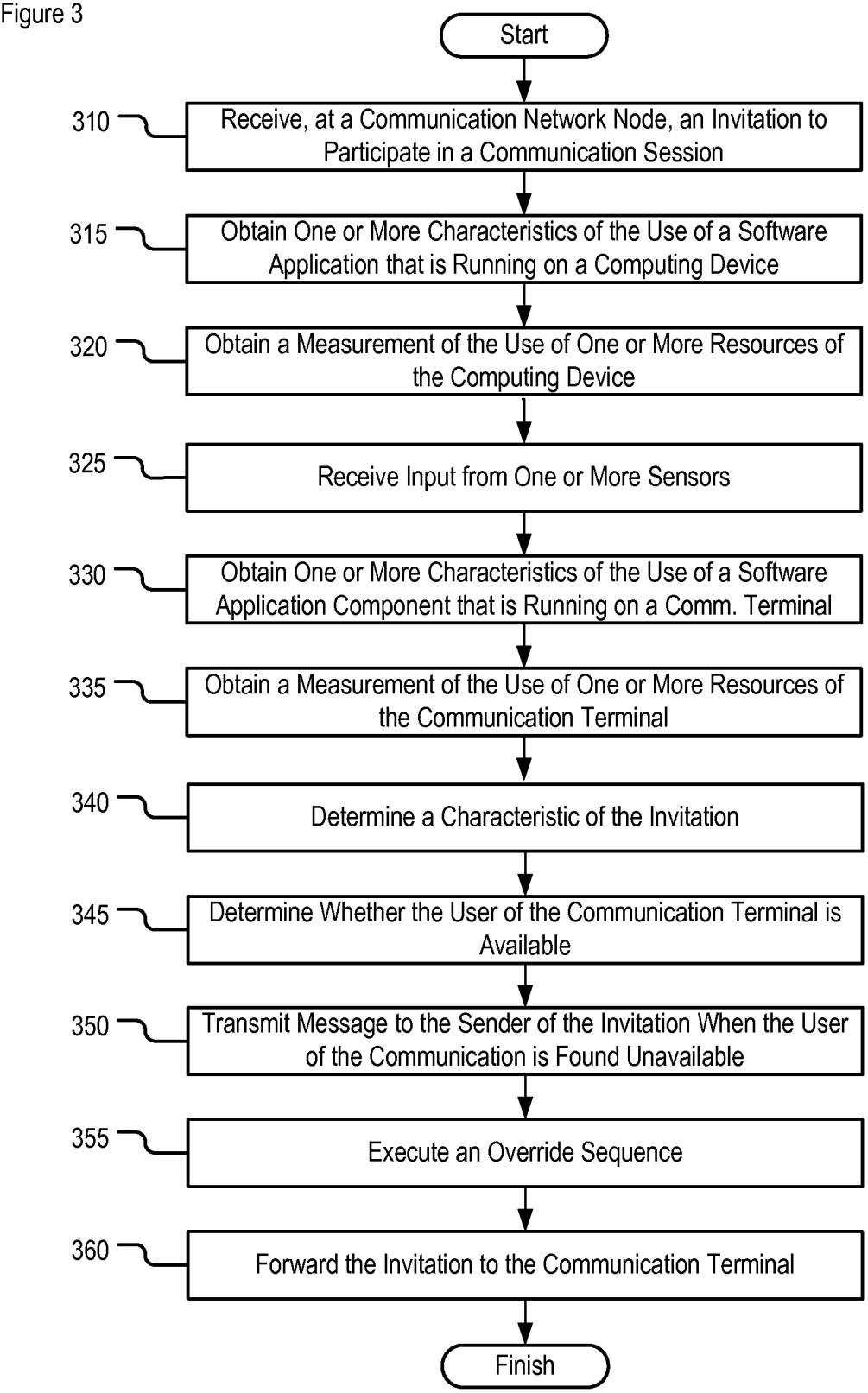
FIG. 3 depicts a flowchart of the execution of the salient tasks associated with the operation of the illustrative embodiment of the present invention.

FIG. 3 depicts a flowchart of the execution of the salient tasks associated with the operation of the illustrative embodiment of the present invention. It will be clear to those skilled in the art, after reading this disclosure, how to perform the tasks associated with FIG. 3 in a different order than represented or to perform one or more of the tasks concurrently. Furthermore, it will be clear to those skilled in the art, after reading this disclosure, how to make and use alternative embodiments of the present invention that omit one or more of the tasks.

At task 310, switch 170 receives an invitation to participate in a communication session. The invitation is transmitted from terminal 110 and is directed to terminal 130-1. In accordance with the illustrative embodiment of the present invention, the communication session is a telephone call. However, it will be clear to those skilled in the art, after reading this disclosure, how to make and use alternative embodiments of the present invention in which the communication session is any other type of communication session, such as, for example, and without limitation, a video call, a chat conversation, teleconference, and others.

At task 315, availability detector 247 obtains a characteristic of the use of a software application that is running on computing device 160-1. In accordance with the illustrative embodiment of the present invention, the characteristic is obtained by computing device monitor 265 and then passed onto monitor client 245 which forwards it to availability detector 247. Although, availability detector 247 obtains a characteristic of the use of a software application, it will be clear to those skilled in the art, after reading this disclosure, how to make and use alternative embodiments of the present invention in which availability detector 247 receives a characteristic of the use of a software application. Task 315 is further described in the discussion with respect to FIG. 4.

At task 320, availability detector 247 obtains a measurement of the use of one or more resources of computing device 160-1. In accordance with the illustrative embodiment of the present invention, the measurement is obtained by computing device monitor 265 and then passed onto monitor client 245 which forwards it to availability detector 247. Task 320 is further described in the discussion with respect to FIG. 5.

At task 325, terminal 130-1 receives input from sensor 150-1. Task 325 is further described in the discussion with respect to FIG. 6.

At task 330, availability detector 247 obtains a characteristic of the use of a software application that is running on terminal 130-1. In accordance with the illustrative embodiment of the present invention, the characteristic is obtained by terminal monitor 235 and then passed onto monitor client 245 which forwards it to availability detector 247. Although, availability detector 247 obtains a characteristic of the use of a software application, it will be clear to those skilled in the art, after reading this disclosure, how to make and use alternative embodiments of the present invention in which availability detector 247 receives a characteristic of the use of a software application component. Task 330 is executed according to the methods described with respect to task 315.

At task 335, availability detector 247 obtains a measurement of the use of one or more resources of terminal 130-1. In accordance with the illustrative embodiment of the present invention, the measurement is obtained by terminal monitor 235 and then passed onto monitor client 245 which forwards it to availability detector 247. Task 335 is executed according to the methods described with respect to task 320.

At task 340, switch 170 determines a characteristic of the invitation to participate in a communication session. Task 340 is further described in the discussion with respect to FIG. 7.

At task 345, switch 170 determines whether the user of terminal 130-1 is available to participate in the communication session for which an invitation is received. Task 345 is further described in the discussion with respect to FIG. 8.

At task 350, switch 170 in a well known fashion transmits a response to the invitation to participate in a communication session. The response is transmitted to terminal 110 if switch 170 determines that the user of terminal 130-1 is unavailable to accept the invitation. In accordance with the illustrative embodiment of the present invention, the response is a rejection. However, it will be clear to those skilled in the art, after reading this disclosure, how to make and use alternative embodiments of the present invention in which a message is transmitted to terminal 110 which identifies an action to be taken by the far-end party, such as, for example, and without limitation, call back later, use another medium of communication, and others. Furthermore, it will be clear to those skilled in the art, after reading this disclosure, how to make and use alternative embodiments of the present invention in which the message contains an indication of additional information concerning the communication session, such as, for example, and without limitation, a preferred communication medium (e.g. voice, text, etc.), preferred alternative time to conduct a communication session, and others.

And still furthermore, it will be clear to those skilled in the art, after reading this disclosure, how to make and use alternative embodiments of the present invention in which switch 170 accepts the call and puts the far-end party on hold. The time for which the far-end party is put on hold can be determined according to an availability policy rule. In further embodiments, the present invention transmits a message to the far-end party indicating that he or she is being put on hold.

At task 355, switch 170 executes an override sequence. The override sequence is executed when switch 170 declines the invitation to participate in a communication session. When this is the case, the user of terminal 110 is given the option to enter a password in order to override the decision of switch 170 and force it to forward the invitation to terminal 130-1. Task 355 is further described in the discussion with respect to FIG. 13.

At task 360, switch 170 forwards the invitation to participate in a communication session to terminal 130-1. Task 360 is executed if switch 170, at task 345, determines that the user of terminal 130-1 is available. Additionally, task 360 is executed as a result of the override sequence execution at task 355.

FIG. 4 depicts a flowchart of the execution of the salient subtasks associated with the performance of task 315. It will be clear to those skilled in the art, after reading this disclosure, how to perform the tasks associated with FIG. 4 in a different order than represented or to perform one or more of the tasks concurrently. Furthermore, it will be clear to those skilled in the art, after reading this disclosure, how to make and use alternative embodiments of the present invention that omit one or more of the tasks.

At task 410, computing device monitor 265 determines the identity of a software application that is executing on computing device 160-1. In accordance with the illustrative embodiment of the present application, computing device monitor 265 determines the identity of the software application by examining log files that are recorded by the operating system of computing device 160-1. However, it will be clear to those skilled in the art, after reading this disclosure, how to make and use alternative embodiments of the present invention in which computing device monitor 265 uses alternative means to determine the identity of the application. In a first alternative embodiment of the present invention, computing device monitor 265 identifies one or more active processes and matches information about the processes (e.g. process name, files associated with the process, etc.) to a specific application.

In a second alternative embodiment of the present invention, computing device monitor 265 identifies patterns of resource consumption and matches these patterns to patterns that are known to be associated with specific applications. For example, and without limitation, the pattern of "85% CPU utilization, 85% memory use" may be associated with a computer game. Whereas the pattern of "25% CPU utilization, 60% cache miss rate" may be associated with a spreadsheet processor. It will be clear to those skilled in the art how to recognize and relate patterns of resource consumption to specific software applications.

Although, at task 410 the illustrative embodiment of the present invention identifies a software application that is being used, it will be clear to those skilled in the art, after reading this disclosure, how to make and use alternative embodiments of the present invention in which the identity of a software application component is determined instead. For example, in a third alternative embodiment of the present invention, terminal monitor 235 determines the identity of a software application component that is executing on terminal 130. In accordance with the third illustrative embodiment of the present invention, the software application is a telephony application which comprises a telephony component and an instant messaging component.

In accordance with the third illustrative embodiment of the present invention, terminal monitor 235 determines what components of the telephony application are used by examining log files that are recorded by the application. However, it will be clear to those skilled in the art, after reading this disclosure, how to make and use alternative embodiments of the present invention in which terminal monitor 235 uses alternative means to determine what application components are used. In one alternative embodiment of the present invention, terminal monitor 235 identifies one or more active processes and matches information about the processes (e.g. process name, files associated with the process, etc.) to a specific application component.

In a fourth alternative embodiment of the present invention, terminal monitor 235 identifies patterns of resource consumption and matches these patterns to patterns that are known to be associated with specific application components. For example, and without limitation, the pattern of "25% CPU utilization" may be associated with the instant messenger component of the telephony application. Whereas the pattern of "50% CPU utilization" may be associated with the telephony component of the application. It will be clear to those skilled in the art how to recognize and relate patterns of resource consumption to specific software components.

At task 420, computing device monitor 265 determines the presence of a keyword in a file that is opened by a software application that is executing on computing device 160-1. In accordance with the illustrative embodiment of the present invention, the software application is a word processor, and the open file is a text document. However, it will be clear to those skilled in the art, after reading this disclosure, how to make and use alternative embodiments of the present invention in which the software application is any other software application that is capable of opening files (e.g. media player, another text editor, file compressing tool, etc.). Furthermore, it will be clear to those skilled in the art, after reading this disclosure, how to make and use alternative embodiments of the present invention in which the open files are of any other type (e.g. MP3, MPEG, JPEG, etc.)

In accordance with the illustrative embodiment of the present invention, computing device monitor 265 locates a document that has a lock placed on it and scans its content for the presence of a keyword. However, it will be clear to those skilled in the art, after reading this disclosure, how to make and use alternative embodiments of the present invention in which computing device monitor 265 locates documents that are open by using alternative means, such as, for example, and without limitation, monitoring system calls made by the software application, examining application log files which indicate what files are opened by the application. Moreover, in the alternative embodiments of the present invention in which the file is a media file, computing device monitor 265 uses voice recognition (or character/image recognition) technology to determine whether the keyword(s) are present in the file.

At task 430, computing device monitor 265 identifies an address to which a software application is (or was) connected. The address is an Internet domain name, but it will be clear to those skilled in the art, after reading this disclosure, how to make and use alternative embodiments of the present invention in which the uniform identifier (URI) is any type of identifier (e.g. Internet Protocol (IP) address, SIP uniform resource identifier (URI), etc.). Furthermore, the software application is an Internet browser, but it will be clear to those skilled in the art, after reading this disclosure, how to make and use alternative embodiments of the present invention in which the software application is any other type of software application (e.g. FTP client, streaming media player, a server, chat client, email client, etc.). In accordance with the illustrative embodiment of the present invention, the address is determined by examining log files that are recorded by the Internet browser. However, it will be clear to those skilled in the art, after reading this disclosure, how to make and use alternative embodiments of the present invention in which the address is identified by alternative means, such as, for example, and without limitation, by examining network traffic, by monitoring the storage of cookies and other tokens on computing device 160-1, etc.

Figure 5:
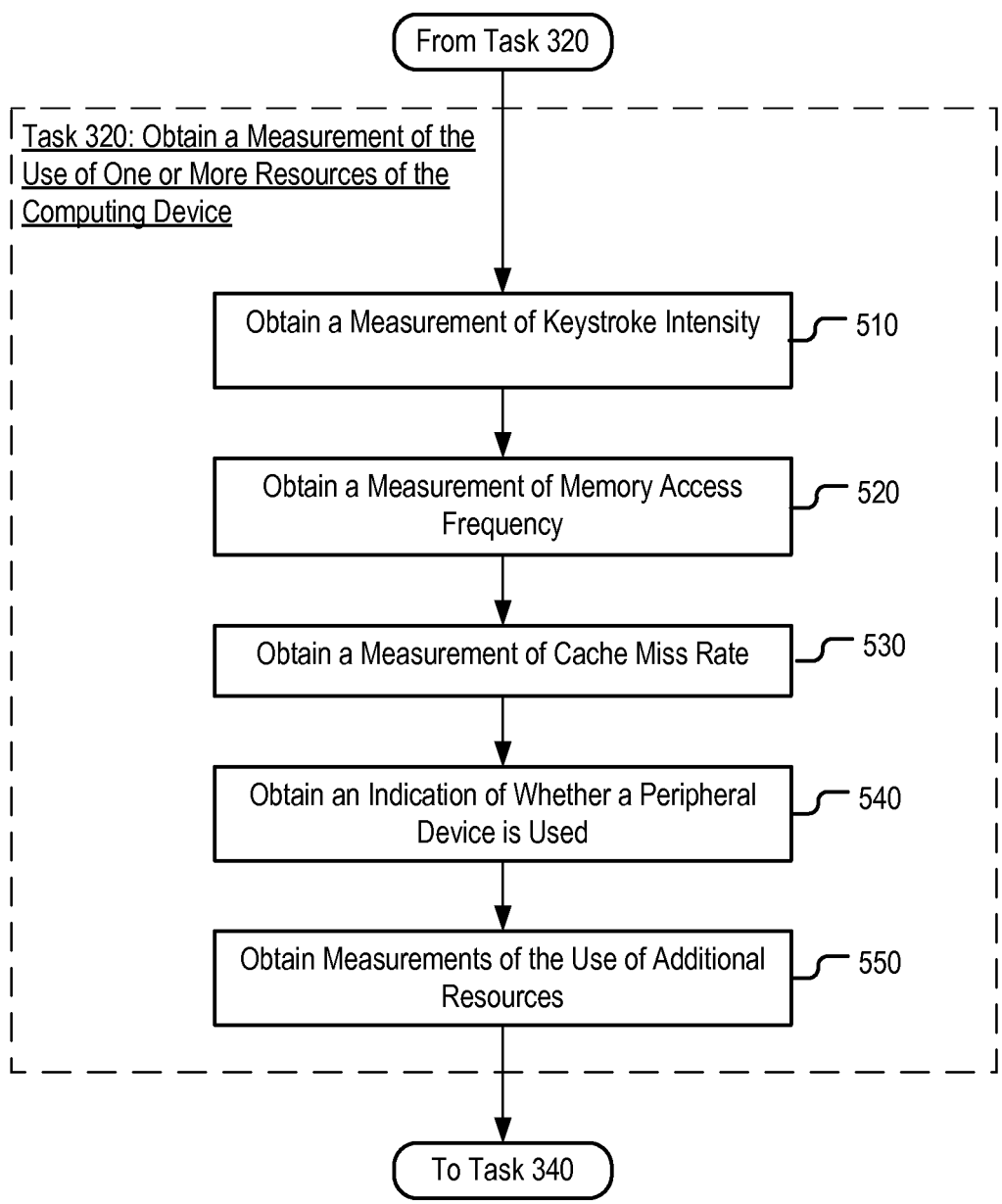
FIG. 5 depicts a flowchart of the execution of the salient subtasks associated with the performance of task 330.

FIG. 5 depicts a flowchart of the execution of the salient subtasks associated with the performance of task 320. It will be clear to those skilled in the art, after reading this disclosure, how to perform the tasks associated with FIG. 5 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 5 describes the taking of measurements of the use of resources of computing device 160-1. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.). It will also be clear to those skilled in the art, after reading this disclosure, that each individual sample can be taken over any time window (i.e. the time period over which the data for an individual sample is collected can vary), such as, for example, and without limitation 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of number of samples, time over which each individual sample is taken, and time period between individual samples can be different for measurements of different resources.

At task 510, computing device monitor obtains a measurement of the keystroke rate for computing device 160-1. A keystroke rate is the rate at which the user of computing device 160-1 presses the keys on the keyboard of the computing device (e.g. 40 keys/minute, etc.).

At task 520, computing device monitor 265 obtains a measure of memory access frequency for computing device 160-1. In accordance with the illustrative embodiment of the present invention, the terminal measures the frequency at which information is requested from the permanent of storage of terminal 160-1. However, it will be clear to those skilled in the art, after reading this disclosure, how to make and use alternative embodiments of the present invention in which the terminal obtains alternative measurements, such as, for example, and without limitation, page fault rate, random access memory write rate, etc.

At task 530, computing device monitor 265 obtains a measurement of the cache miss rate for the processor of computing device 160-1.

At task 540, computing device monitor 265 determines whether a peripheral device is used by computing device 160-1. In accordance with the illustrative embodiment, the peripheral device is a scanner, but it will be clear to those skilled in the art, after reading this disclosure, how to make and use alternative embodiments of the present invention in which the use of another peripheral device is detected, such as, for example, and without limitation, printer, slide presentation remote control, microphone, audio speakers, video camera, headphones, etc.

At task 550, computing device monitor 265 obtains measurements of the use of additional hardware resources of computing device 160-1. In accordance with the illustrative embodiment the present invention, computing device monitor 265 determines processor temperature, video card (or GPU) temperature, video card memory use, whether video card 3D acceleration is used, whether surround sound capabilities of a sound adapter are used, sound adapter utilization, processor temperature, etc.

Figure 6:
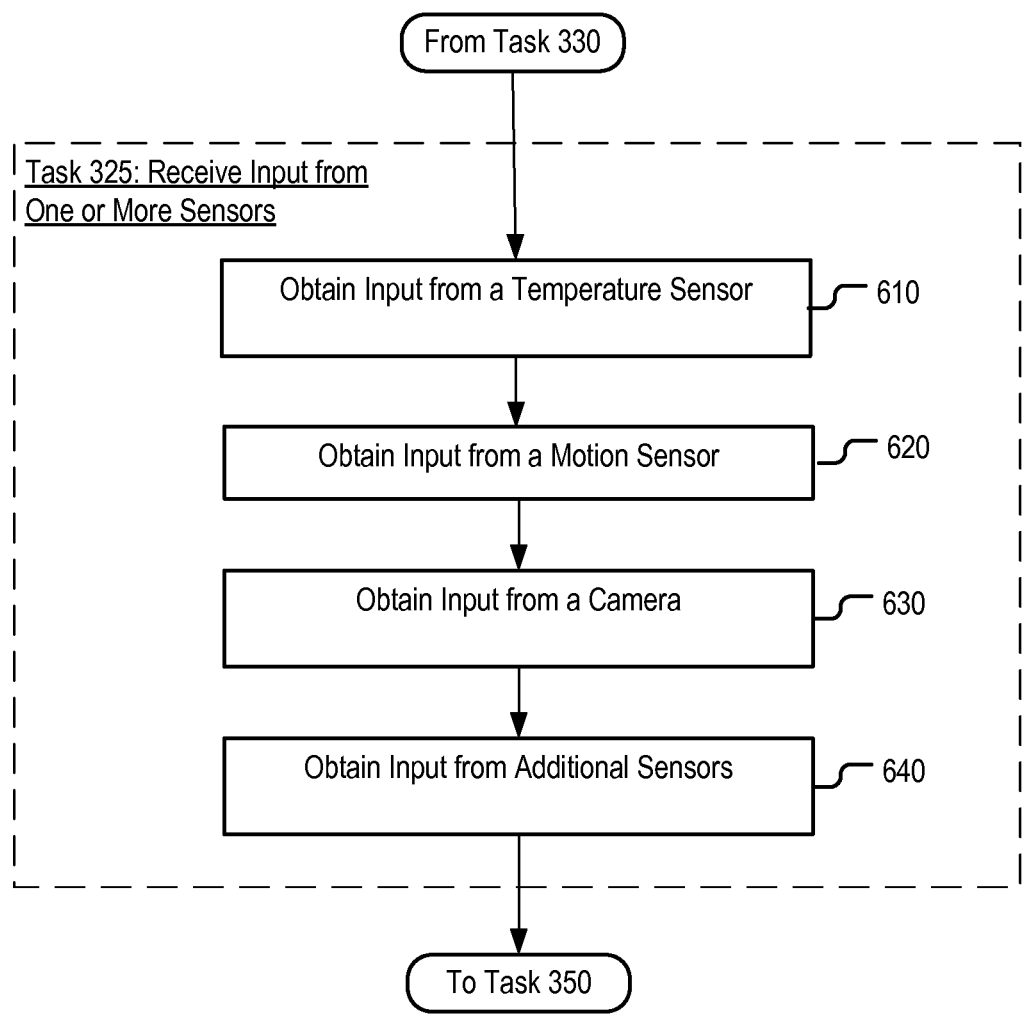
FIG. 6 depicts a flowchart of the execution of the salient subtasks associated with the performance of task 340.

FIG. 6 depicts a flowchart of the execution of the salient subtasks associated with the performance of task 325. It will be clear to those skilled in the art, after reading this disclosure, how to perform the tasks associated with FIG. 6 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 6 describes the taking of measurements from different sensors. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.). It will also be clear to those skilled in the art, after reading this disclosure, that each individual sample can be taken over any time window (i.e. the time period over which the data for an individual sample is collected can vary), such as, for example, and without limitation, 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of: number of samples, time over which each individual sample is taken, and time period between individual samples can be different for measurements from different sensors.

At task 610, availability detector 247 obtains a temperature measurement from temperature sensor 251. It will be clear to those skilled in the art how to execute task 610.

At task 620, availability detector 247 obtains a measurement from motion sensor 252.

At task 630, availability detector 247 obtains input from camera 253. In accordance with the illustrative embodiment of the present invention, the camera input is used to determine whether a user is standing in the camera's range of vision. However it will be clear to those skilled in the art, after reading this disclosure, how to make and use alternative embodiments of the present invention in which availability detector 247 applies image recognition technologies such as, for example and without limitation, facial recognition, facial expression recognition, and gaze direction recognition.

At task 640, availability detector 247 obtains input from additional sensors, such as, for example, and without limitation, appliance sensors (i.e. sensors that detect whether a particular appliance such as a kitchen stove is running), barometric pressure sensors, humidity sensors, pressure sensors, sensors that measure physiological parameters (e.g. ECG, EEG, etc.), and others.

Figure 7:
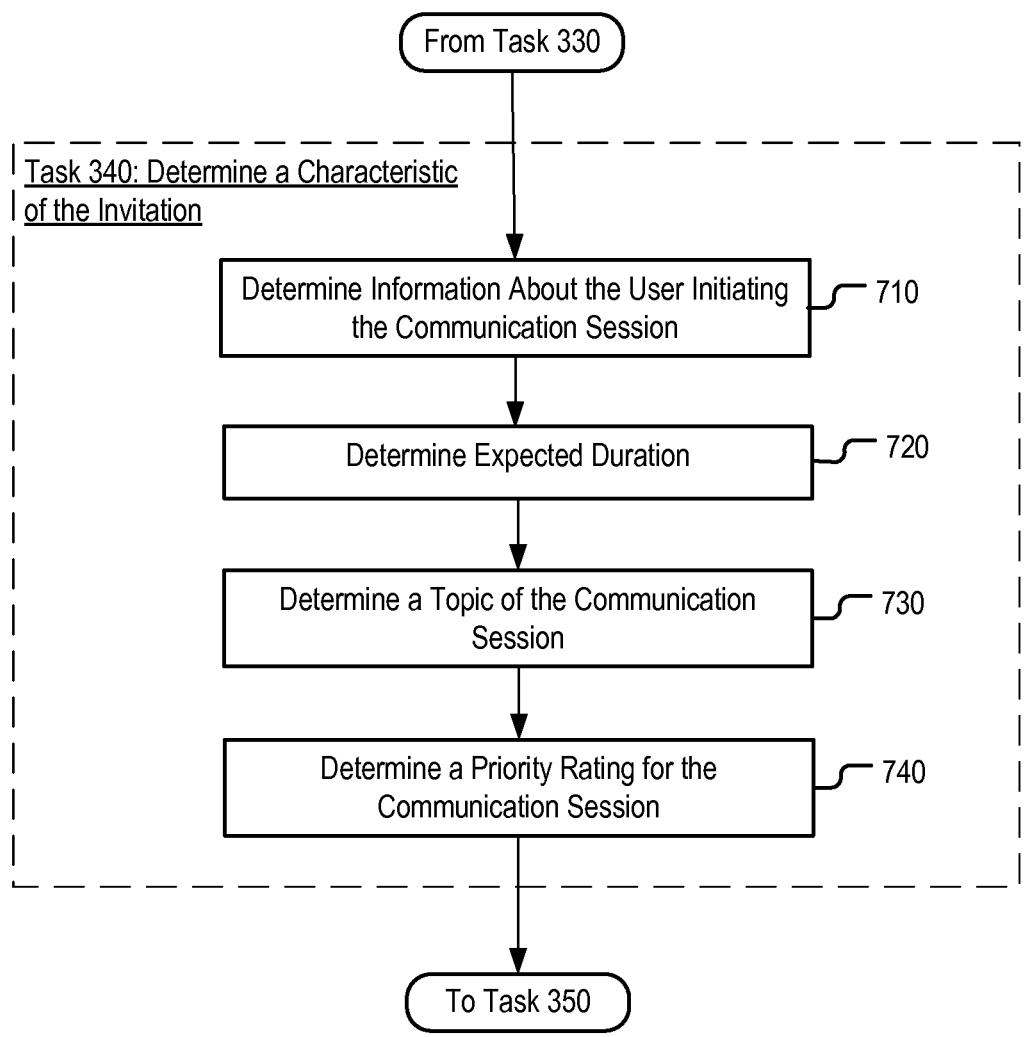
FIG. 7 depicts a flowchart of the execution of the salient subtasks associated with the performance of task 350.

FIG. 7 depicts a flowchart of the execution of the salient subtasks associated with the performance of task 340. It will be clear to those skilled in the art, after reading this disclosure, how to perform the tasks associated with FIG. 7 in a different order than represented or to perform one or more of the tasks concurrently. Furthermore, it will be clear to those skilled in the art, after reading this disclosure, how to make and use alternative embodiments of the present invention that omit one or more of the tasks.

At task 710, availability detector 247 obtains information about the user initiating the communication session. In accordance with the illustrative embodiment of the present invention, availability detector 247 determines the endpoint identifier of the terminal from which the communication session is initiated. However, it will be clear to those skilled in the art, after reading this disclosure, how to make and use alternative embodiments of the present invention in which availability detector 247 determines the identity of the person making the telephone call by using an identification technology, such as Caller ID or by doing a reverse telephone number lookup in a telephone directory.

It will also be clear to those skilled in the art, after reading this disclosure, how to make and use alternative embodiments of the present invention in which availability detector 247 determines additional information about the person initiating the communication session, such as, for example, and without limitation, rank within a company (e.g. CEO, director of department, etc.), gender, age, employment status, social security number, etc. The alternative embodiments of the present invention obtain the additional information by performing a database search with a search key that is based on the endpoint identifier of terminal 110. However, it will be clear to those skilled in the art, after reading this disclosure, how to make and use further alternative embodiments of the present invention in which the additional information is contained in the invitation itself or contained in a separate message that is received by availability detector 247.

Furthermore, it will be clear to those skilled in the art, after reading this disclosure, how to make and use alternative embodiments of the present invention, in which a relationship between the user initiating the communication session and the user of the terminal to which the invitation to participate in a communication session is addressed—terminal 130-1, is obtained or determined (e.g. the caller is the supervisor of the user of terminal 130-1, the caller is a relative of the user of terminal 231-1, etc.). In some alternative embodiments of the present invention, the relationship information is received at switch 170 along with the invitation to participate in a communication session. In other embodiments of the present invention, the relationship between the caller and the user of terminal 130-1 is derived from the identity information of the caller and tables that relate the caller to the user (e.g. employee records, family records, etc.).

At task 720, availability detector 247 determines the expected duration of the communication session. Availability detector 247 searches a call log for information about the duration of past communication sessions between the terminal to which the invitation to participate in a communication session is addressed—terminal 130-1, and terminal 110 and calculates the expected duration of the communication session for which an invitation is received. In accordance with the illustrative embodiment of the present invention, the expected duration is the average of the n most recent communication sessions, where 17 is an integer.

Furthermore, it will be clear to those skilled in the art, after reading this disclosure, how to make and use alternative embodiments of the present invention in which the expected duration is contained in the invitation itself (e.g. the content of the ANI field or an equivalent is overwritten, etc.). And still furthermore, it will be clear to those skilled in the art, after reading this disclosure, how to make and use alternative embodiments of the present invention in which the expected duration is received at terminal 130-1 in a message that is separate from the invitation.

At task 730, availability detector 247 determines the topic of the communication session. In accordance with the illustrative embodiment of the present invention, an indication of the topic is contained in the invitation itself (e.g. the content of the ANI field or an equivalent is overwritten, etc.). However, it will be clear to those skilled in the art, after reading this disclosure, how to make and use alternative embodiments of the present invention in which an indication of the topic is received in a message that is separate from the invitation.

At task 740, availability detector 247 determines a priority rating for the communication session. In accordance with the illustrative embodiment of the present invention, one of three ratings is chosen: "important," "extremely important," and "not important." However, it will be clear to those skilled in the art, after reading this disclosure, how to make and use alternative embodiment of the present invention in which the space of possible ratings is either larger or smaller.

In accordance with the illustrative embodiment of the present invention, an indication of the priority rating is contained in the invitation itself (e.g. the content of the ANI field or an equivalent is overwritten, etc.). However, it will be clear to those skilled in the art, after reading this disclosure, how to make and use alternative embodiments of the present invention in which an indication of the priority rating is received in another message that is separate from the invitation. Furthermore, it will be clear to those skilled in the art, after reading this disclosure, how to make and use alternative embodiments of the present invention in which the importance rating is determined by availability detector 247 on the basis of information received at tasks 710 through 730 (e.g. if the CEO of a company call, the priority rating is set to "extremely important," the priority rating is set to "important" if the topic is "accounting," etc.).

Figure 8:
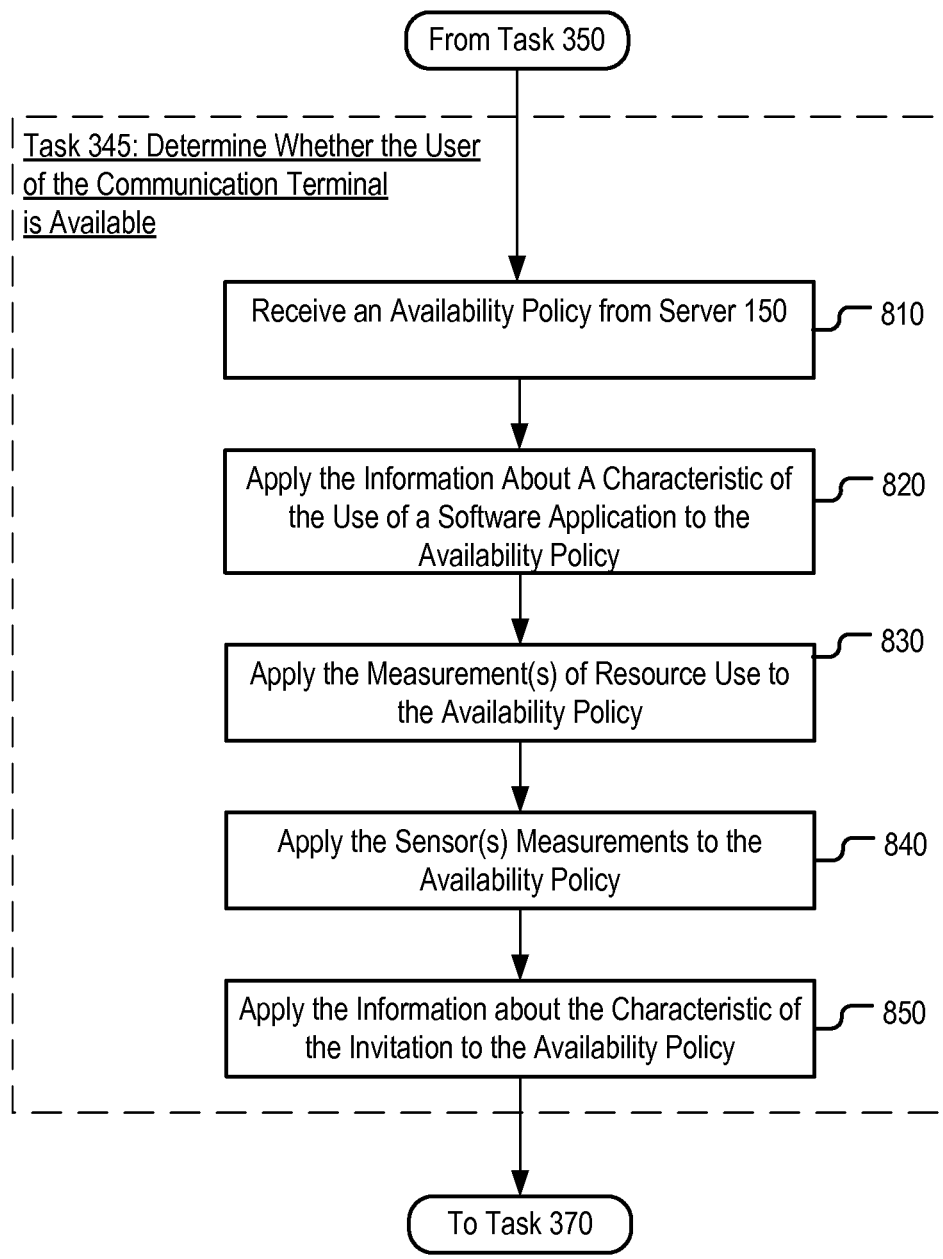
FIG. 8 depicts a flowchart of the execution of the salient subtasks associated with the performance of task 360.

FIG. 8 depicts a flowchart of the execution of the salient subtasks associated with the performance of task 345. It will be clear to those skilled in the art, after reading this disclosure, how to perform the tasks associated with FIG. 8 in a different order than represented or to perform one or more of the tasks concurrently. Furthermore, it will be clear to those skilled in the art, after reading this disclosure, how to make and use alternative embodiments of the present invention that omit one or more of the tasks.

At task 810, availability detector 247 receives an availability policy from server 150. As previously noted, for the purposes of this Specification, the term "availability policy" is defined as a set of one or more rules which determine when a user is available for communications. In accordance with the illustrative embodiment of the present invention, the policy is received in an extensible markup language (XML) file, but it will be clear to those skilled in the art, after reading this disclosure, how to make and use alternative embodiments of the present invention in which the policy is represented in any other form, such as, for example, a text file, a sequence of numbers, etc. Although, in accordance with the illustrative embodiment of the present invention, the policy is obtained from a server, it will be clear to those skilled in the art, after reading this disclosure, how to make and use alternative embodiments of the present invention in which the policy is stored on terminal 130-1.

More specifically, at task 810, the present invention receives an availability policy which comprises four rules for determining whether a user is available. These rules are:
 i. "user is unavailable if the weighed sum of availability scores assigned to web sites which the user recently visited is below fifty-five (55),"
 ii. "user is unavailable if the weighted sum of the five most recent samples of the user's keystroke rate exceeds one-hundred and thirty (130),"
 iii. "user is unavailable if the temperature in the office of the user is below fifty-five-degrees Fahrenheit (55 F)," and
 iv. "user is available if the CEO of a company calls."

In accordance with the illustrative embodiment of the present invention, the availability policy rules specify whether a user is to accept an incoming invitation to participate in a communication session. However, it will be clear to those skilled in the art, after reading this disclosure, how to make and use alternative embodiments of the present invention in which the availability policy rules specify other aspects of a user's availability, such as, for example, and without limitation, an alternative communication medium, alternative time to call, time delay for which the far-end party is to be put on hold, etc.

In the alternative embodiments of the present invention in which availability policy rules are used to select a preferred medium of communication on which the user is available, the rules depend on one or more of a characteristic of the use of a software application that is executing on computing device 160-1 and/or terminal 130-1, a measurement of the use of one or more resources of computing device 160-1 and/or terminal 130-1, input from one or more sensors, a characteristic of a software application component that is executing on terminal 130-1, and a characteristic of the invitation. Examples of such rules include:
 i. "notify far-end party that text is a preferred medium of communication if the keystroke rate of the user of computing device 160-1 exceeds eighty (80) characters per minute,"
 ii. "notify far-end party that voice is a preferred medium of communication if the user is using the chat component of a telephony application that is running on availability detector 247."

In the alternative embodiments of the present invention in which the incoming invitation to participate in a communication session is accepted, but put on hold, the time period for which the session is held idle is determined in accordance with one or more availability policy rules. The availability policy rules in these alternative embodiments depend on one or more of a characteristic of the use of a software application that is executing on computing device 160-1 and/or terminal 130-1, a measurement of the use of one or more resources of computing device 160-1 and/or terminal 130-1, input from one or more sensors, a characteristic of a software application component that is executing on terminal 130-1, and a characteristic of the invitation. Examples of such rules include:
 i. "put the session on hold for n minutes, if the measured keystroke rate is between fifty (50) and eighty (80) strokes per minute,"
 ii. "put the session on hold until the keystroke falls below a threshold (e.g. 50 keystrokes),"
 iii. "put the session on hold until a input from one or more sensors falls below a threshold (e.g. motion sensor indicates that a user has stopped moving intensely)," and
 vi. "put the session on hold until the user of computing device 160-1 stops using a specific software application."

It will be clear to those skilled in the art, after reading this disclosure, how to make and use alternative embodiments of the present invention in which tasks 330 through 360 are executed repeatedly, after the far-end party is put on hold, until availability detector 247 determines that a condition which determines whether a user is to be taken off hold has been fulfilled.

Furthermore, it will be clear to those skilled in the art, after reading this disclosure, how to make and use alternative embodiments of the present invention, in which switch 170 initially declines the invitation to participate the communication session from terminal 110, but continues to execute tasks 230 through 260 repeatedly until the user of terminal 130-1 becomes available, as determined according to an availability rule. When the user becomes available, switch 170 initiates a new communication session and connects terminal 130-1 to terminal 110.

For example, and without limitation, in one alternative embodiment of the present invention, tasks 230 through 260 are executed until the user's keystroke intensity falls below a threshold, such as fifty keystrokes per minute. In this alternative embodiment of the present invention, the availability rule provides that a user is available if the user's keystroke rate is under fifty keystrokes per minute. Thus, when the user's keystroke rate falls below the threshold, switch 170 initiates a new communication session and connects terminal 130-1 to terminal 110.

In the alternative embodiments of the present invention in which availability policy rules are used to determine an alternative time for the far end party to call, the rules depend on one or more of a characteristic of the use of a software application that is executing on computing device 160-1 and/or terminal 130-1, a measurement of the use of one or more resources of computing device 160-1 and/or terminal 130-1, input from one or more sensors, a characteristic of a software application component that is executing on terminal 130-1, and a characteristic of the invitation. Examples of such rules include:
 i. "if cache miss rate exceeds fifty percent (50%), ask far-end party to call back in 90 minutes,"
 ii. "if the movie player component of a multimedia player application is used, ask far-end party to call in a predetermined period of time (e.g. 120 minutes)."

In accordance with the alternative embodiments of the present invention, the call-back time period is provided in the policy rule used to determine availability. However, it will be clear to those skilled in the art, after reading this disclosure, how to make and use alternative embodiments of the present invention in which the call-back time period is determined according to appointment information that is stored as a database entry on one of switch 170, terminal 130-1, 130-2, 130-3, 130-4, and server 140 (e.g. information stored by calendar applications, etc.).

Although, in accordance with the illustrative embodiment of the present invention, the availability policy rules are neutral with respect to the time at which the communication session is received or the medium of the communication session, it will be clear to those skilled in the art, after reading this disclosure, how to make and use alternative embodiments of the present invention in which the rules depend on the time at which the invitation to participate on the communication session is received or the medium of the communication session. Examples of such rules include:
  i. "user is unavailable if the invitation to participate in a communication session is received within a specific time period;"
  ii. "user is available if the medium for the communication session is text;"
  iii. user is unavailable if the medium for the communication session is voice.

At task 820, availability detector 247 applies the first rule to the information obtained at task 320. Although, the first rule depends on the recent web site visits, it will be clear to those skilled in the art, after reading this disclosure, how to make and use alternative embodiments of the present invention in which the first rule depends on any type of information that is received at task 315 and/or task 330 (e.g use of specific components of software, presence of keywords, etc.) Task 820 is further described in the discussion with respect to FIG. 9 and FIG. 10.

At task 830, availability detector 247 applies the second rule to the information obtained at task 320. Although, the second rule depends on keystroke intensity measurements, it will be clear to those skilled in the art, after reading this disclosure, how to make and use alternative embodiments of the present invention in which the second rule depends on any type of information that is received at task 320 and/or task 335 (e.g. measurements of memory access rate, cache miss rate, information whether a peripheral device is used, etc.) Task 830 is further described in the discussion with respect to FIG. 11.

At task 840, availability detector 247 applies the third rule to the information that is received at task 325. Although, the third rule depends on a temperature measurement, it will be clear to those skilled in the art, after reading this disclosure, how to make and use alternative embodiments of the present invention in which the third rule depends on any type of information that is collected at task 325 (e.g. motion sensor input, camera input, etc.). Task 840 is further described in the discussion with respect to FIG. 12.

At task 850, availability detector 247 applies the fourth rule to the information that is obtained at task 340. In accordance with the rule, if the user which initiated the communication session is the CEO of a company, availability detector 247 accepts the invitation. Although, the fourth rule depends on the position of the calling party within a company, it will be clear to those skilled in the art, after reading this disclosure, how to make and use alternative embodiments of the present invention in which the fourth rule depends on any information that is obtained at task 340. For example, and without limitation, such alternative rules include:
  i. "user is always available if the priority rating of the invitation is "extremely important," and
  ii. "the user is always available if the expected duration for the communication session is less than a predetermined threshold (e.g. 5 minutes)."

It will also be clear to those skilled in the art, after reading this disclosure, how to make and use alternative embodiments of the present invention in which the rule depends on a relationship, which is determined at task 710, between the calling party and the user of terminal 130-1. For example, and without limitation, such rules include:
  i. "user is always available if a relative of the user calls"
  ii. "user is always available if someone who is higher up in the user's company calls."

Figure 9:
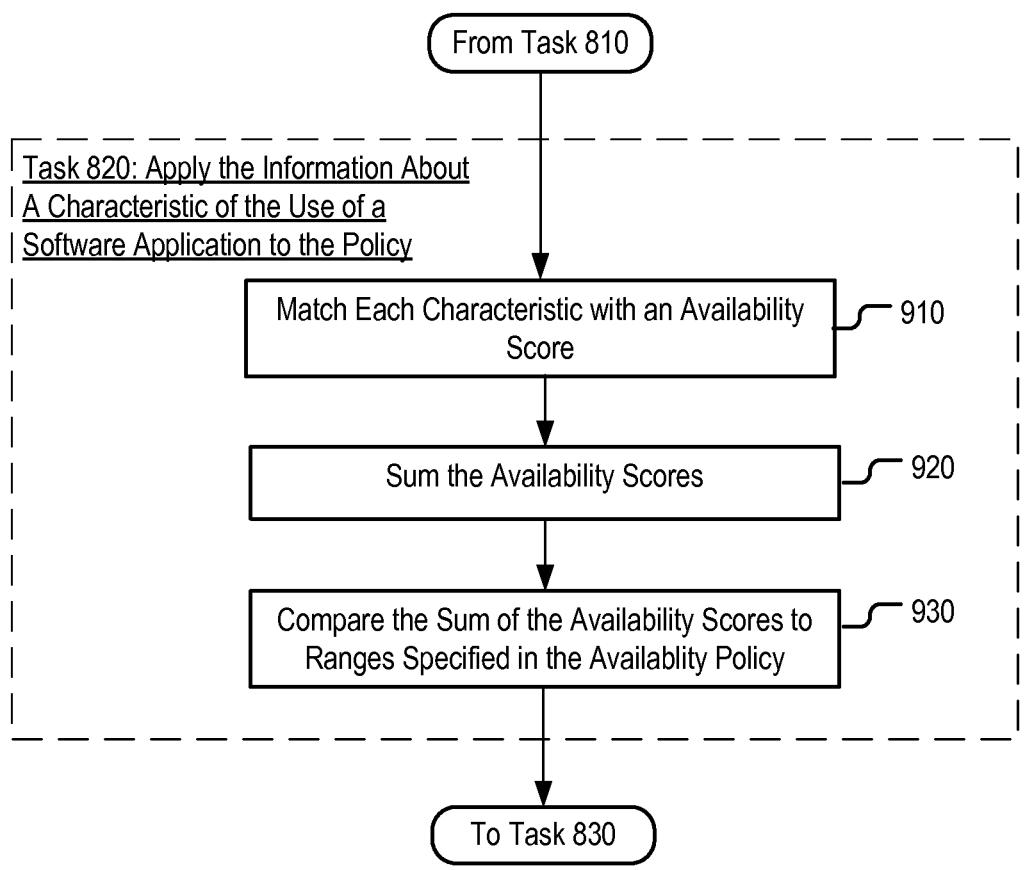
FIG. 9 depicts a flowchart of the execution of the salient subtasks associated with the performance of task 820.

FIG. 9 depicts a flowchart of the execution of the salient subtasks associated with the performance of task 820. It will be clear to those skilled in the art, after reading this disclosure, how to perform the tasks associated with FIG. 9 in a different order than represented or to perform one or more of the tasks concurrently. Furthermore, it will be clear to those skilled in the art, after reading this disclosure, how to make and use alternative embodiments of the present invention that omit one or more of the tasks.

At tasks 910 through 930, availability detector 247 applies the first policy rule received at task 810. The first policy rule provides that a user is unavailable if the weighed sum of availability scores assigned to web sites which the user recently visited is less than fifty-five (55). Although, the availability policy rule depends on keystroke rate, it will be clear to those skilled in the art, after reading this disclosure, how to make and use alternative embodiments of the present invention in which the availability policy rule depends on any information that is obtained at tasks 315 and 330.

Availability scores are numbers which are used in determining whether the user of terminal 130-1 is available to participate in communications. In accordance with the illustrative embodiment of the present invention, the availability scores are contained in the indication of the policy received at task 810 (e.g. the XML file), however, those skilled in the art will readily recognize, after reading this disclosure, how to make and use alternative embodiments of the present invention in which the availability scores are separated from the availability policy, such as, for example, and without limitation, embodiments in which the availability scores are stored on terminal 130-1 or on a remote server.

At task 910, availability detector 247 matches a characteristic with an availability score. Furthermore, in accordance with a first illustrative embodiment of the present invention, the following set of availability scores is made available for uniform resource identifiers (URIs) that were visited by computing device 160-1:

TABLE 1

Availability Scores Assigned to Uniform Resource Identifiers

| Uniform Resource Identifier (URI) | Availability Score |
|---|---|
| Movies.com TM | 10 |
| Bloomberg.com TM | 40 |
| Internal_document_repository | 85 |

As noted, the availability score is an indication of the likelihood that the user of terminal 130-1 is not available to accept the incoming invitation. In accordance with the illustrative embodiment of the present invention, the magnitude of the availability score is inversely proportional to the probability that the user is available to respond to the invitation received at task 310. Furthermore, in accordance with the illustrative embodiment of the present invention, "Movies.com™" is assigned a low availability score. The rationale for assigning the low score is that Movies.com™ is a website that is usually viewed for personal entertainment. In contrast, the internal document repository, in this illustrative embodiment, is a document storage location which is used strictly for business. If the user is visiting the document repository, he or she is most likely to be engaged in performing tasks related to the user's employment. For this reason, the internal document repository is assigned a high availability score.

In accordance with an alternative embodiment of the present invention, the following availability scores are assigned to keywords that are found in documents that are opened for editing:

TABLE 2

Availability Scores Assigned to Keywords

| Keywords | Availability Score |
|---|---|
| "LOL" | 15 |
| "fiscal year" | 40 |
| "project deadline" | 85 |

In accordance with the second embodiment of the present invention, the word "LOL" is assigned a low priority score. "LOL" is an abbreviation for "laughing out loud" and is a common element of Internet slang. When this word is present in a document, the user of terminal 130-1 is likely engaged in a personal conversation. Consequently, the keyword "LOL" assigned a low availability score.

In accordance with the second alternative embodiment of the present invention, two types of documents are scanned for keywords by availability detector 247:
  i. documents which are open by the user of terminal 130-1 for editing, and
  ii. documents which are open by a software application for editing as a result of a user's interaction with the software application, such as a message log which is open as a consequence of a user sending an instant message, possibly, without the user being aware of its opening.

However, it will be clear to those skilled in the art, after reading this disclosure, how to make and use alternative embodiments of the present invention in which only one of the two types of documents is scanned.

At task 920, availability detector 247 calculates the sum of the availability scores identified at task 910. It will be clear to those skilled in the art, after reading this disclosure, how to make and use alternative embodiments of the present invention in which availability detector 247 calculates an alternative number, such as, for example, and without limitation, a weighted sum, weighted average, the average of the scores, and others.

At task 930, availability detector 247 matches the calculated sum to a predetermined range defined in the policy received at task 810. In accordance with the illustrative embodiment of the present invention, the policy provides that if the sum is less than fifty-five (55), the user of terminal 130-1 is available to accept the invitation to participate in a communication session.

Figure 10:
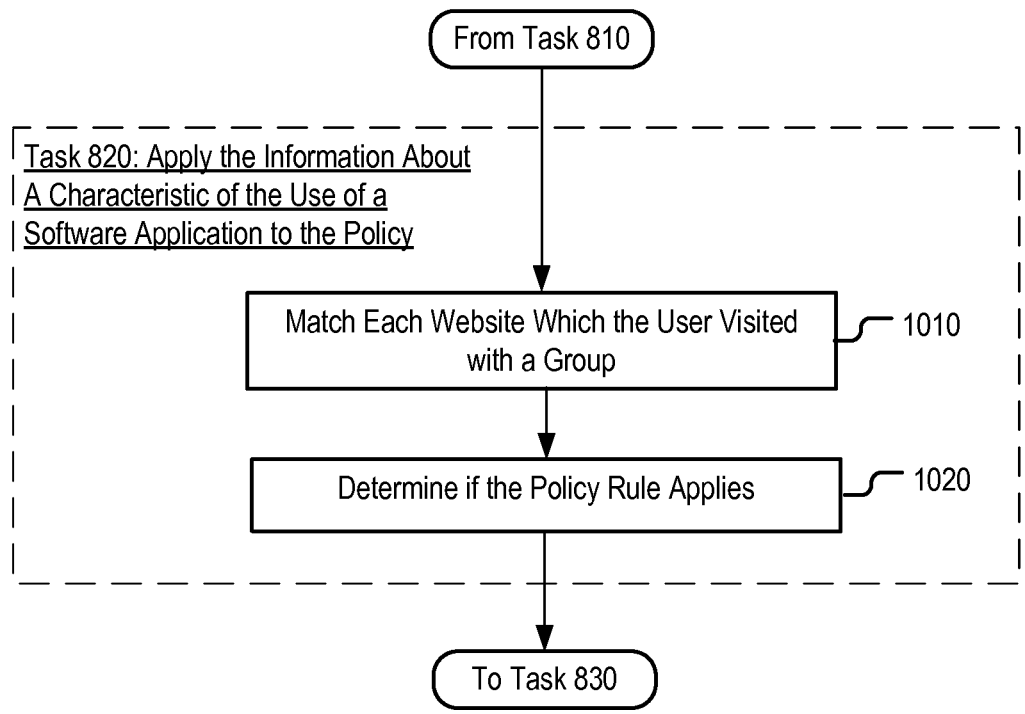
FIG. 10 depicts a flowchart of the execution of the salient subtasks associated with the performance of task 820 as performed by another illustrative embodiment of the present invention.

FIG. 10 depicts a flowchart of the execution of the salient subtasks associated with the performance of task 820 as performed by another illustrative embodiment of the present invention. It will be clear to those skilled in the art, after reading this disclosure, how to perform the tasks associated with FIG. 10 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1010 and 1020, availability detector 247 applies a policy rule. The policy rule provides that a user is unavailable if the number of websites from a "business" group, which the user visited, is more than or equal to the number of visited websites from a "personal entertainment" group.

In accordance with this illustrative embodiment of the present invention, the websites visited are classified into groups. The group definitions are contained in the policy received at task 810 (e.g. the XML file), but those skilled in the art will readily recognize, after reading this disclosure, how to make and use alternative embodiments of the present invention in which the group definitions are stored on terminal 130-1 or on a remote server.

At task 1010, availability detector 247 determines the groups for the last three web sites that were most recently visited by an Internet browser executing on computing device 160-1. The three websites are "Movies.com™," "Bloomberg.com™," and "internal document repository." The group definitions for the illustrative embodiment of the present invention are listed below:

TABLE 3

Web Site Group Definitions

| Business Websites | Entertainment Websites | News Websites |
|---|---|---|
| Internal document repository | Youtube.com TM | Bloomberg.com TM |
| Corporation web site | Movies.com TM | Cnn.com TM |
| A client web site | Netflix.com TM | News.com TM |
| Another client's website | Cinema.com TM | bbc.com TM |

It will be clear to those skilled in the art, after reading this disclosure, how to make and use alternative embodiments of the present invention in which the group definitions are different. Those skilled in the art will readily recognize, after reading this disclosure that the group definitions depend on the application for which the invention is used.

At task 1020, availability detector 247 determines whether the policy rule applies. Since Movies.com™ belongs to the entertainment group, the internal document repository belongs to the business group, and Bloomberg.com™ belongs to neither of the "business" and "entertainment" groups," the number of "business" websites visited by the user is more than or equal to the number of "entertainment" web sites. Therefore, in accordance with the availability policy rule of this embodiment, the user is found available to participate in a communication session.

Figure 11:
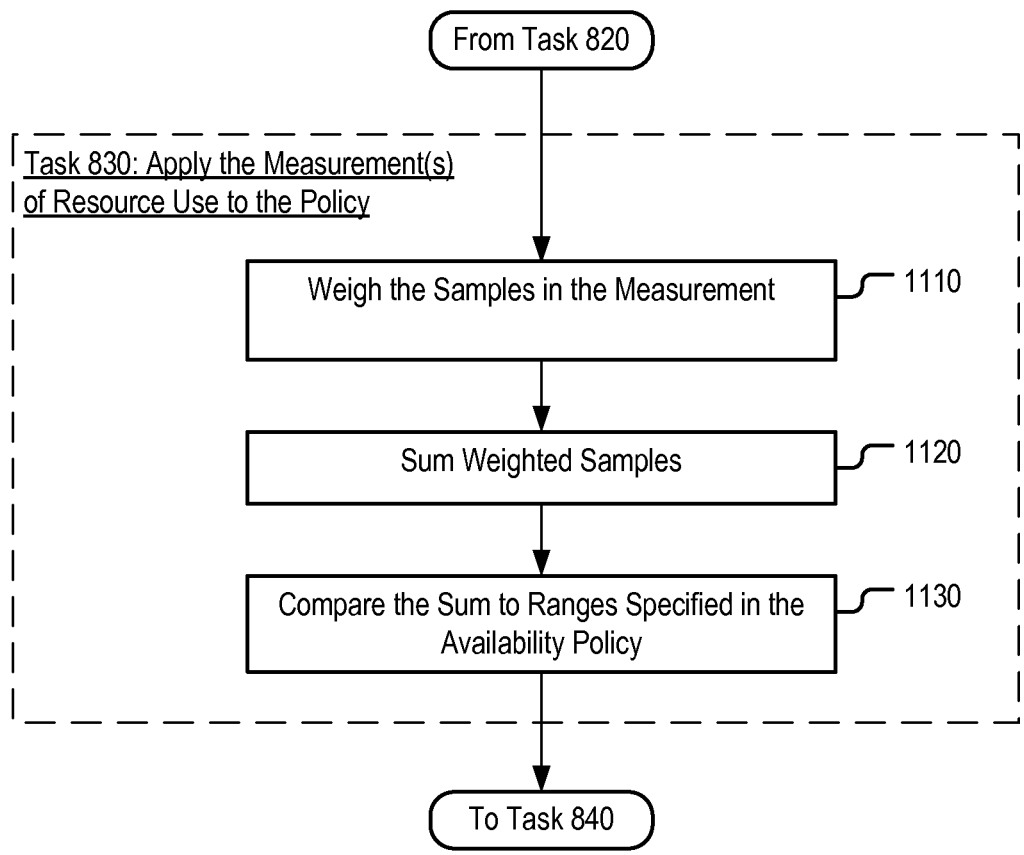
FIG. 11 depicts a flowchart of the execution of the salient subtasks associated with the performance of task 830.

FIG. 11 depicts a flowchart of the execution of the salient subtasks associated with the performance of task 830. It will be clear to those skilled in the art, after reading this disclosure, how to perform the tasks associated with FIG. 11 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1110 through 1130, availability detector 247 applies the second policy rule received at task 810 to the information received at task 320. The second policy rule provides that a user is unavailable if the weighted sum of the five most recent samples of the user's keystroke rate exceeds one-hundred and thirty (130).

At task 1110, availability detector 247 weights the samples in the measurements of the use of resources of computing device 160-1 which were obtained at task 320. In accordance with the illustrative embodiment of the present invention, availability detector 247 receives a measurement of the rate at which keys on its keyboard are struck (i.e. keystroke rate).

Availability detector 247 receives the data samples contained in the first two rows of Table 4:

TABLE 4

Keystroke Samples and Corresponding Weight Values

| | Sample (keystrokes/minute) | | | | |
|---|---|---|---|---|---|
| | 45 | 80 | 55 | 32 | 65 |
| Time at Which the Sample is Taken | $t_0$ | $t_1$ | $t_2$ | $t_3$ | $t_4$ |
| Weight Coefficient | 1 | .85 | .75 | .60 | .45 |

In accordance with the illustrative embodiment of the present invention, each sample is multiplied to the weight coefficient in order to derive the weighted value of this sample. The samples are weighted according to the time at which they are taken (e.g. the more recent samples are weighted less). It will be clear to those skilled in the art how to assign appropriate weight values. Furthermore, it will be clear to those skilled in the art, after reading this disclosure, how to make and use alternative embodiments of the present invention in which the samples are not weighted.

At task 1120, availability detector 247 calculates the sum of the weighted samples.

At task 1130, availability detector 247 matches the calculated sum to a predetermined range defined in the policy received at task 810. In accordance with the illustrative embodiment of the present invention, the policy provides that if the sum of the weighted keystroke rate samples is less than 130, the user of terminal 130-1 is available to accept the invitation to participate in a communication session. Although, the policy is based on a plurality of keystroke rate samples, it will be clear to those skilled in the art, after reading this disclosure, how to make and use alternative embodiments of the present invention in which the policy depends on a single sample (e.g. "user is unavailable if keystroke rate is greater than eighty (80) characters per minute), on the weighted average of the samples or any other combination of the samples.

Although, the policy rule of the illustrative embodiment of the present invention depends on keystroke rate, it will be clear to those skilled in the art, after reading this disclosure, how to make and use alternative embodiments of the present invention in which the availability policy rule depends on the use of other resources measured at tasks 320 and 335 (e.g. both keystroke rate and cache miss rate, etc.). Examples of such rules are:

i. "user is unavailable when cache miss rate exceeds fifty percent (50%);"
  ii. "user is available if less than ten (10) read requests to a permanent storage device are made in the past minute;"
  iii. "user is unavailable if a scanner connected to computing device 160-1 is being used at the time at which the invitation to participate in a communication session is received."

It will be clear to those skilled in the art, after reading this disclosure how to make and use alternative embodiments of the present invention in which the ranges for availability and unavailability differ from the illustrative embodiment. It will be clear to those skilled in the art, after reading this disclosure, how to assign values to the ranges. Furthermore, it will be clear to those skilled in the art, after reading this disclosure, how to make and use alternative embodiments of the present invention, in which a third range is specified and when the sum falls into the third range, a message is transmitted from terminal 130-1 to terminal 110 asking the user of terminal 110 to call back in a predetermined period of time (e.g. 30 minutes).

Figure 12:
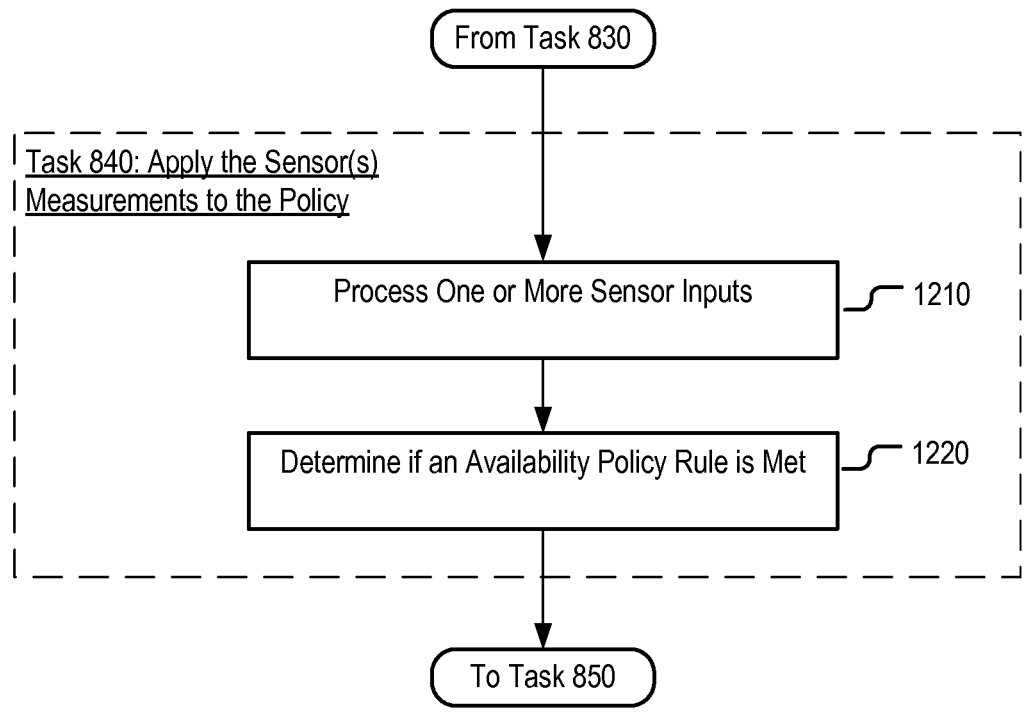
FIG. 12 depicts a flowchart of the execution of the salient subtasks associated with the performance of task 840.

FIG. 12 depicts a flowchart of the execution of the salient subtasks associated with the performance of task 840. It will be clear to those skilled in the art, after reading this disclosure, how to perform the tasks associated with FIG. 12 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1210 through 1230, availability detector 247 applies the third policy rule received at task 810 to the information received at task 325. The third policy rule provides that a user is unavailable if the temperature in the office of the user is below fifty-five degrees Fahrenheit (55 F).

At task 1210, availability detector 247 processes the sensor input received at task 240. In accordance with the illustrative embodiment of the present invention, availability detector 247 digitizes (when analog signal is received) and normalizes the sensor data received at task 325. Although, in accordance with the illustrative embodiment of the present invention, input from a temperature sensor is processed, it will be clear to those skilled in the art, after reading this disclosure, how to make and use alternative embodiments of the present invention in which input from other sensors (e.g. motion sensors, physiological sensors, humidity sensors, etc.) is processed in the same fashion.

In accordance with one alternative embodiment of the present invention, availability detector 247 processes the camera input received at task 630 to determine the mood of the user. Specifically, the terminal uses a mood detector that employs facial recognition. However, it will be clear to those skilled in the art, after reading this disclosure, how to make and use alternative embodiments of the present invention in which input from physiological sensors (e.g. ECG and ECG) is also used in assessing the mood of the user of terminal 130-1.

At task 1220, availability detector 247 determines whether the input from a temperature sensor received at task 325 indicates that the temperature is below fifty-five degrees Fahrenheit (55F).

In accordance with the alternative embodiment of the present invention, availability detector 247 applies the results from the mood detection to a policy which relates users' mood to their availability. Furthermore, in accordance with the alternative embodiment of the present invention, the policy provides that the incoming invitation should be accepted only when the mood detection concludes that the user of terminal 130-1 is in a positive mood.

Figure 13:
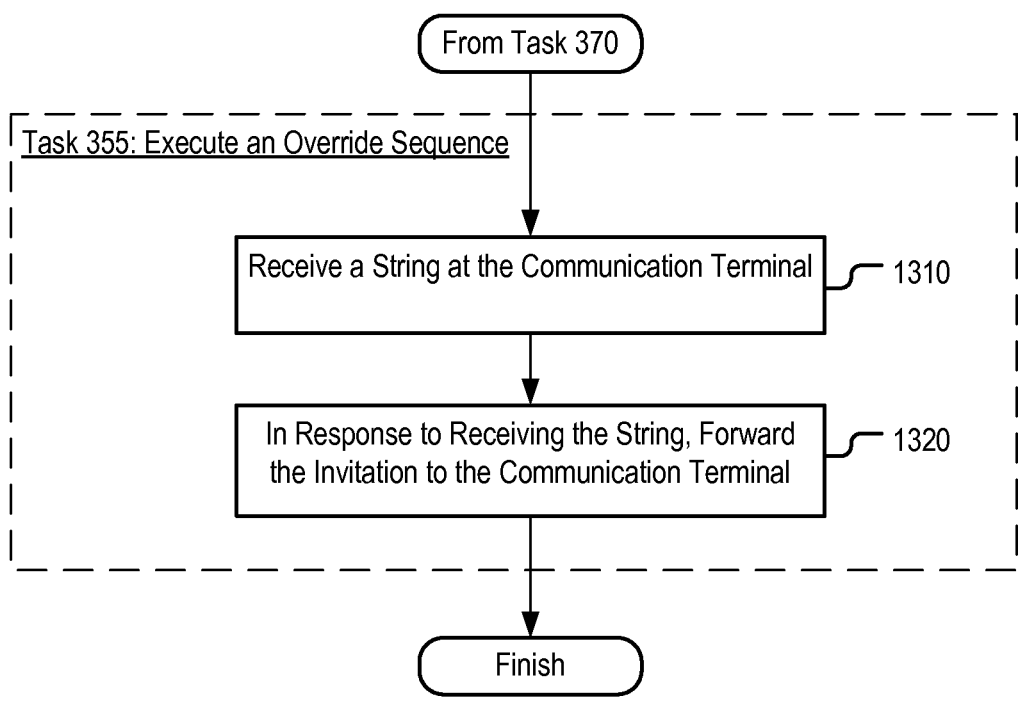
FIG. 13 depicts a flowchart of the execution of the salient subtasks associated with the performance of task 380.

FIG. 13 depicts a flowchart of the execution of the salient subtasks associated with the performance of task 355. It will be clear to those skilled in the art, after reading this disclosure, how to perform the tasks associated with FIG. 13 in a different order than represented or to perform one or more of the tasks concurrently. Furthermore, it will be clear to those skilled in the art, after reading this disclosure, how to make and use alternative embodiments of the present invention that omit one or more of the tasks.

At task 1310, switch 170 receives a string from terminal 110. In accordance with the illustrative embodiment of the present invention, the string is alphanumerical, but it will be clear to those skilled in the art, after reading this disclosure, that the string can be of any type (e.g. numerical, etc.)

At task 1320, availability detector 247 compares the received to the string to a second string which is stored on switch 170. If the two strings match, availability detector 247 causes terminal switch 170 to forward the invitation to terminal 130-*i*. It will be clear to those skilled in the art, after reading this disclosure, how to make and use alternative embodiments of the present invention in which the string is stored on a remote server and not on switch 170. Furthermore, it will be clear to those skilled in the art, after reading this disclosure, how to make and use alternative embodiments of the present invention in which the second string is specified by the policy received at task 810. And still furthermore, it will be clear to those skilled in the art, after reading this disclosure, how to make and use alternative embodiments of the present invention in which the policy received at task 810 provides whether availability detector 247 should accept the call even if the two strings match (i.e. the policy provides whether the override component of the present invention is enabled).

Figure 14:
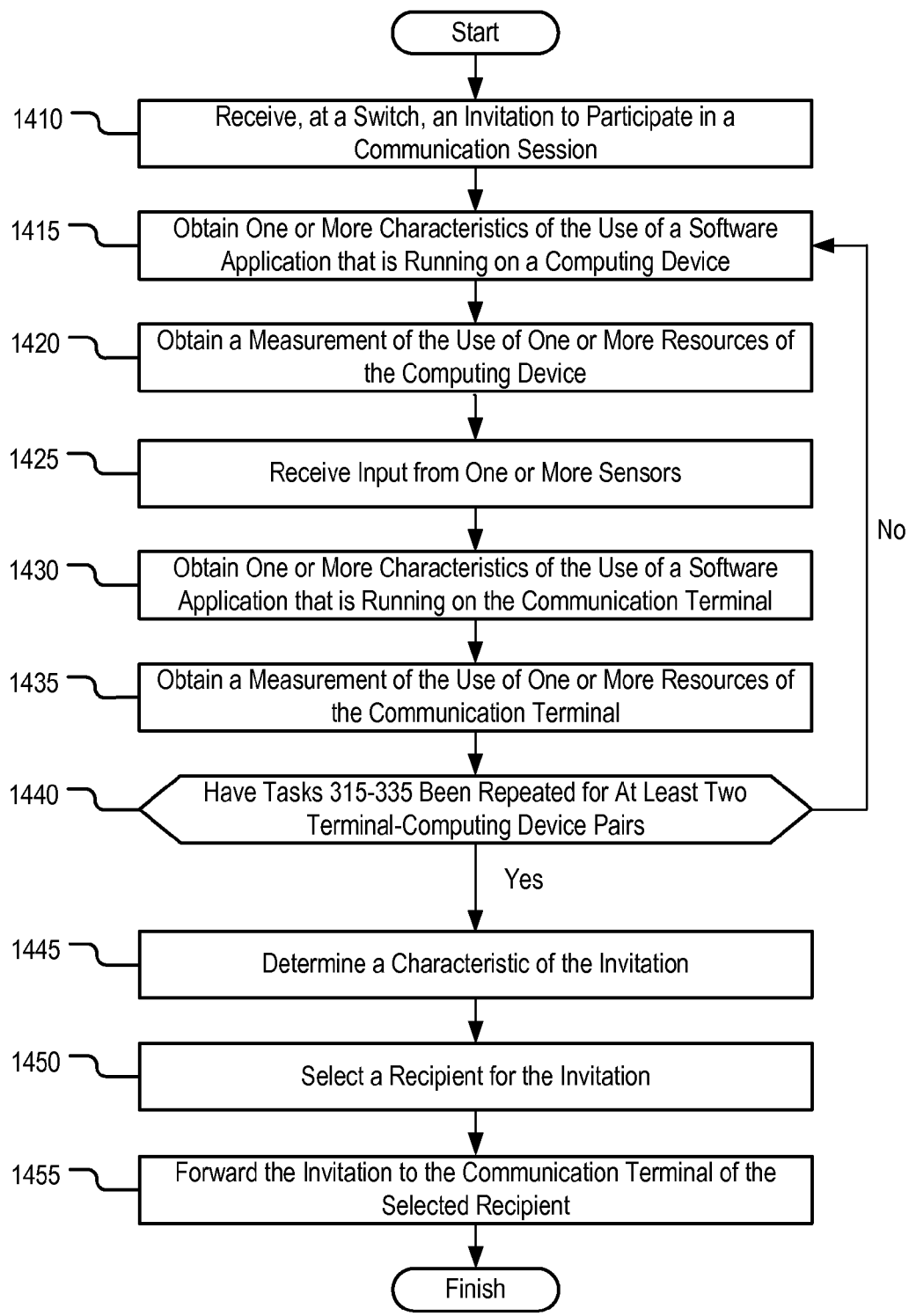
FIG. 14 depicts a flowchart of the execution of the salient tasks associated with the operation of the illustrative embodiment of the present invention.

FIG. 14 depicts a flow chart of the execution of the salient tasks associated with the operation of the illustrative embodiment of the present invention.

At task 1410, switch 170 receives an invitation to participate in a communication session from terminal 110.

At task 1415, recipient selector 249 obtains a characteristic of the use of a software application that is running on computing device 160-*i*. Although, in accordance with the illustrative embodiment of the present invention, recipient selector 249 receives a characteristic of the use of a software application, it will be clear to those skilled in the art, after reading this disclosure, how to make and use alternative embodiments of the present invention in which recipient selector 249 receives a characteristic of the use of a software application component. In accordance with the illustrative embodiment of the present invention, the characteristic is obtained by computing device monitor 265 and then passed onto monitor client 245 which forwards it to recipient selector 249.

At task 1420, recipient selector 249 obtains a measurement of the use of one or more resources of computing device 160-*i*. In accordance with the illustrative embodiment of the present invention, the measurement is obtained by computing device monitor 265 and then passed onto monitor client 245 which forwards it to recipient selector 249.

At task 1425, terminal 130-1 receives input from sensor 150-1. Task 1425 is identical to task 325.

At task 1430, recipient selector 249 obtains a characteristic of the use of a software application that is running on terminal 130-1. Although, in accordance with the illustrative embodiment of the present invention, recipient selector 249 receives a characteristic of the use of a software application, it will be clear to those skilled in the art, after reading this disclosure, how to make and use alternative embodiments of the present invention in which recipient selector 249 receives a characteristic of the use of a software application component. In accordance with the illustrative embodiment of the present invention, the characteristic is obtained by terminal monitor 235 and then passed onto monitor client 245 which forwards it to recipient selector 249. Task 1430 is identical to task 330.

At task 1435, recipient selector 249 obtains a measurement of the use of one or more resources of terminal 130-*i*. In accordance with the illustrative embodiment of the present invention, the measurement is obtained by terminal monitor 235 and then passed onto monitor client 245 which forwards it to recipient selector 249. Task 1435 is identical to task 335.

At task 1440, recipient selector 249 determines whether tasks 1410-1435 have been executed for all communication terminals 130-*i* and all computing devices 160-*i* to which switch 170 is connected. If the tasks have been executed for all devices, availability detector 247 executes task 1445. Otherwise, tasks 1415-1435 are executed again. Although, in accordance with the illustrative embodiment of the present invention, information about all devices that are connected to switch 170 is obtained, it will be clear to those skilled in the art, after reading this disclosure, how to make and use alternative embodiments of the present invention in which information for a subset of the devices connected to switch 170 is obtained.

At task 1445, recipient selector 249 obtains a characteristic of the invitation to participate in a communication session. Task 1445 is identical to task 340.

At task 1450, recipient selector 249 selected a recipient for the invitation to participate in the communication session. The recipient is selected in accordance with a routing policy that is retrieved from server 140. Task 1450 is further described in the discussion with respect to FIG. 15.

At task 1455, recipient selector 249 transmits the invitation to the selected recipient.

Figure 15:
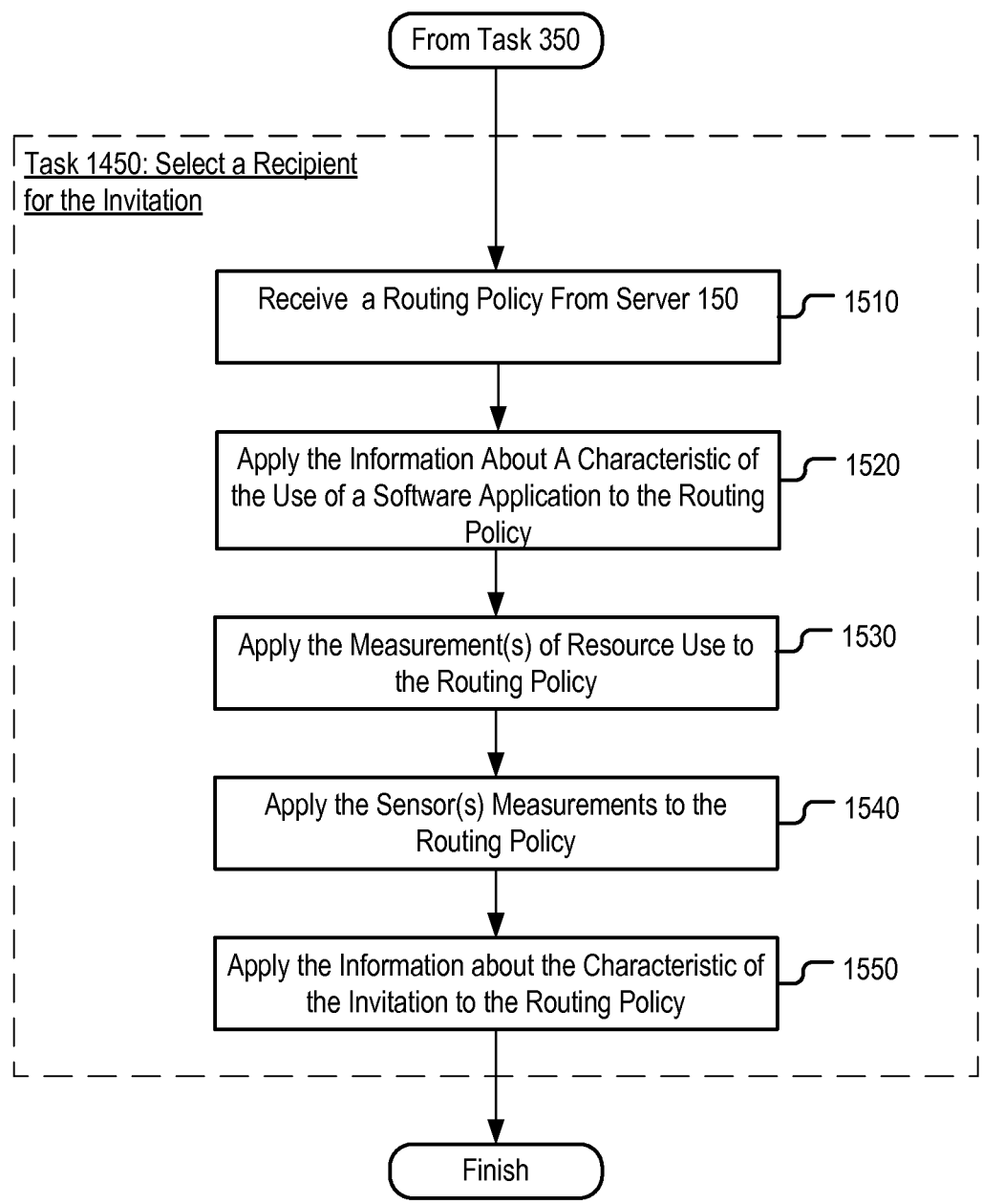
FIG. 15 depicts a flowchart of the execution of the salient subtasks associated with the performance of task 1450.

FIG. 15 depicts a flowchart of the execution of the salient subtasks associated with the performance of task 1450. It will be clear to those skilled in the art, after reading this disclosure, how to perform the tasks associated with FIG. 15 in a different order than represented or to perform one or more of the tasks concurrently. Furthermore, it will be clear to those skilled in the art, after reading this disclosure, how to make and use alternative embodiments of the present invention that omit one or more of the tasks.

At task 1510, recipient selector 249 receives an routing policy from server 150. As previously noted, for the purposes of this specification, the term "routing policy" is defined as a set of one or more rules which determine how an invitation for a communication session is to be routed. In accordance with the illustrative embodiment of the present invention, the policy is received in an extensible markup language (XML) file, but it will be clear to those skilled in the art, after reading this disclosure, how to make and use alternative embodiments of the present invention in which the policy is represented in any other form, such as, for example, a text file, a sequence of numbers, etc. Although, in accordance with the illustrative embodiment of the present invention, the policy is obtained from a server, it will be clear to those skilled in the art, after reading this disclosure, how to make and use alternative embodiments of the present invention in which the policy is stored on switch 170 or terminal 130-1.

More specifically, at task 1510, the present invention receives a routing policy which comprises four rules for selecting a recipient for the communication session invitation. These rules are:
  i. "select the user that has the highest weighed sum of availability scores assigned to web sites which the user recently visited,"
  ii. "select the user with the lowest keystroke rate,"
  iii. "select a user that shifts the least in his or he seat," and
  iv. "select the highest ranked user."

At task 1520, recipient selector 249 applies the first rule to the information obtained at task 1415. Although, the first rule depends on the recent web site visits, it will be clear to those skilled in the art, after reading this disclosure, how to make and use alternative embodiments of the present invention in which the first rule depends on any type of information that is received at task 1415 and/or task 1430 (e.g use of specific components of software, presence of keywords, etc.) Task 1520 is executed according to the methods described in the discussion with respect to task 820.

At task 1530, recipient selector 249 applies the second rule to the information obtained at task 1420. Although, the second rule depends on keystroke intensity measurements, it will be clear to those skilled in the art, after reading this disclosure, how to make and use alternative embodiments of the present invention in which the second rule depends on any type of information that is received at task 1420 and/or task 1435 (e.g. measurements of memory access rate, cache miss rate, information whether a peripheral device is used, etc.) Task 1530 is executed according to the methods described in the discussion with respect to task 830.

At task 1540, recipient selector 249 applies the third rule to the information that is received at task 1425. Although, the third rule depends on information from a motion sensor, it will be clear to those skilled in the art, after reading this disclosure, how to make and use alternative embodiments of the present invention in which the third rule depends on any type of information that is collected at task 340 (e.g. temperature sensor input, camera input, etc.). Task 1540 is executed according to the methods described in the discussion with respect to task 840.

At task 1550, recipient selector 249 applies the fourth rule to the information that is obtained at task 340. In accordance with the rule, the highest ranked user among the users of communication terminals 130-*i* is selected. For example, if the user of terminal 130-1 is project manager in a company and the user of terminal 130-2 is a head of department in the company, the latter is selected. Although, the fourth rule depends on the position of the calling party within a company, it will be clear to those skilled in the art, after reading this disclosure, how to make and use alternative embodiments of the present invention in which the fourth rule depends on any information that is obtained at task 1435. Task 1550 is executed according to the methods described in the discussion with respect to task 850.

It is to be understood that the disclosure teaches just examples of the illustrative embodiments and that many variations of the invention can easily be devised by those skilled in the art after reading this disclosure and that the scope of the present invention is to be determined by the following claims.

What is claimed is:

1. A method comprising:
    receiving, at a communication network node, an invitation for a communication session;
    determining, via a processor, whether a recipient is available to accept the communication session, based on a characteristic of a use of a component of a software application by the recipient; and
    when the recipient is available:
        (1) selecting the recipient among a plurality of potential recipients to receive the invitation; and
        (2) forwarding the invitation from the communication network node to a communication terminal associated with the recipient.

2. The method of claim 1, wherein the software application is executing on a computing device that is associated with the communication terminal.

3. The method of claim 1, wherein the software application is executing on the communication terminal, and the component of the software application is not needed by the communication terminal for the conduct of the communication session for which an invitation is received.

4. The method of claim 1, wherein the characteristic of the use of the component of the software application comprises a Uniform Resource Identifier to which the software application established a connection.

5. The method of claim 1, wherein the characteristic of the use of the component of the software application comprises a presence of a keyword.

6. The method of claim 1, wherein the characteristic of the use of the component of the software application comprises an indication that the first component is open for editing by the software application.

7. A system comprising:
    a processor; and
    a computer-readable storage device storing instructions which, when executed by the processor, cause the processor to perform operations comprising:
        receiving, at a communication network node, an invitation for a communication session;
        determining whether a recipient is available to accept the communication session, based on a characteristic of a use of a component of a software application by the recipient; and
        when the recipient is available:
            (1) selecting the recipient among a plurality of potential recipients to receive the invitation; and
            (2) forwarding the invitation from the communication network node to a communication terminal associated with the recipient.

8. The system of claim 7, wherein the software application is executing on a computing device that is associated with the communication terminal.

9. The system of claim 7, wherein the software application is executing on the communication terminal, and the component of the software application is not needed by the communication terminal for the conduct of the communication session for which an invitation is received.

10. The system of claim 7, wherein the characteristic of the use of the component of the software application comprises a Uniform Resource Identifier to which the software application established a connection.

11. The system of claim 7, wherein the characteristic of the use of the component of the software application comprises a presence of a keyword.

12. The system of claim 7, wherein the characteristic of the use of the component of the software application comprises an indication that the first component is open for editing by the software application.

13. A computer-readable storage device storing instructions which, when executed by a processor, cause the processor to perform operations comprising:
    receiving, at a communication network node, an invitation for a communication session;
    determining whether a recipient is available to accept the communication session, based on a characteristic of a use of a component of a software application by the recipient; and
    when the recipient is available:
        (1) selecting the recipient among a plurality of potential recipients to receive the invitation; and
        (2) forwarding the invitation from the communication network node to a communication terminal associated with the recipient.

14. The computer-readable storage device of claim 13, wherein the software application is executing on a computing device that is associated with the communication terminal.

15. The computer-readable storage device of claim 13, wherein the software application is executing on the communication terminal, and the component of the software application is not needed by the communication terminal for the conduct of the communication session for which an invitation is received.

16. The computer-readable storage device of claim 13, wherein the characteristic of the use of the component of the software application comprises a Uniform Resource Identifier to which the software application established a connection.

17. The computer-readable storage device of claim 13, wherein the characteristic of the use of the component of the software application comprises a presence of a keyword.

18. The computer-readable storage device of claim 13, wherein the characteristic of the use of the component of the software application comprises an indication that the first component is open for editing by the software application.

* * * * *